(12) United States Patent
van Ryper et al.

(10) Patent No.: US 8,067,245 B2
(45) Date of Patent: Nov. 29, 2011

(54) AUTOMATED MICROSCOPE FOR BLOOD CELL ANALYSIS

(75) Inventors: William John van Ryper, Menomonie, WI (US); Tyler Cote, Chelmsford, MA (US); Steven I. Small, Medfield, MA (US); Amy P. Sheng, Somerville, MA (US); Ivan Hee Yiu Ma, San Mateo, CA (US); Ronald Jones, Newtown, NH (US)

(73) Assignee: Medica Corporation, Bedford, MA (US)

( * ) Notice: Subject to any disclaimer, the term of this patent is extended or adjusted under 35 U.S.C. 154(b) by 785 days.

(21) Appl. No.: 11/492,372

(22) Filed: Jul. 24, 2006

(65) Prior Publication Data

US 2008/0020128 A1 Jan. 24, 2008

(51) Int. Cl.
*G01N 1/00* (2006.01)

(52) U.S. Cl. ............ 436/174; 436/180; 422/63; 422/64; 422/65; 422/66; 422/67; 422/563; 359/391

(58) Field of Classification Search .................. 436/174, 436/180; 422/63–67, 99–100, 563; 359/391
See application file for complete search history.

(56) References Cited

U.S. PATENT DOCUMENTS

| | | | |
|---|---|---|---|
| 4,224,032 A * | 9/1980 | Glover et al. .................... | 436/46 |
| 4,989,253 A * | 1/1991 | Liang et al. .................... | 381/110 |
| 5,016,173 A | 5/1991 | Kenet et al. | |
| 5,386,318 A * | 1/1995 | Kuhnert et al. ............... | 359/394 |
| 5,428,690 A * | 6/1995 | Bacus et al. ................... | 382/128 |
| 5,499,097 A | 3/1996 | Ortyn et al. | |
| 5,690,892 A | 11/1997 | Babler et al. | |
| 5,793,969 A | 8/1998 | Kamentsky et al. | |
| 5,822,447 A | 10/1998 | Kasdan | |
| 6,101,265 A | 8/2000 | Bacus et al. | |
| 6,151,405 A | 11/2000 | Douglass | |
| 6,215,892 B1 | 4/2001 | Douglass | |
| 6,404,916 B1 | 6/2002 | De La Torre-Bueno | |
| 6,418,236 B1 | 7/2002 | Ellis | |
| 6,718,053 B1 | 4/2004 | Ellis | |
| 2002/0176160 A1 * | 11/2002 | Suzuki et al. ................. | 359/380 |

FOREIGN PATENT DOCUMENTS

WO    WO/2005/082508    9/2005

* cited by examiner

*Primary Examiner* — Jyoti Nagpaul
(74) *Attorney, Agent, or Firm* — Kristofer E. Elbing

(57) ABSTRACT

An apparatus and method of automated blood cell analysis uses technologies from other systems to create a new, robust, improved type of automated microscope, which uses electronic motors and a closed loop control system to minimize ambient factors, such as jarring and temperature changes. Pre-stained blood smear slides are first coated with a thin film of oil and are loaded into a carousel from which they can individually be analyzed. The slides are moved under a low magnification microscope; an optimal area of examination is determined; a focal plane map is calculated for that area, and the positions of white blood cell candidates are computed. The slide is then moved under a high power microscope where a refined focal plane map is computed and the individual white blood cell candidates are imaged. The cells are preclassified and the images are made available for analysis by the technician. Additionally, samples of red blood cells, equivalent to what the technician would do manually, are imaged and presented to the technician for evaluation. The technician may make notes on those cells, both red and white blood cells and archive them.

18 Claims, 23 Drawing Sheets

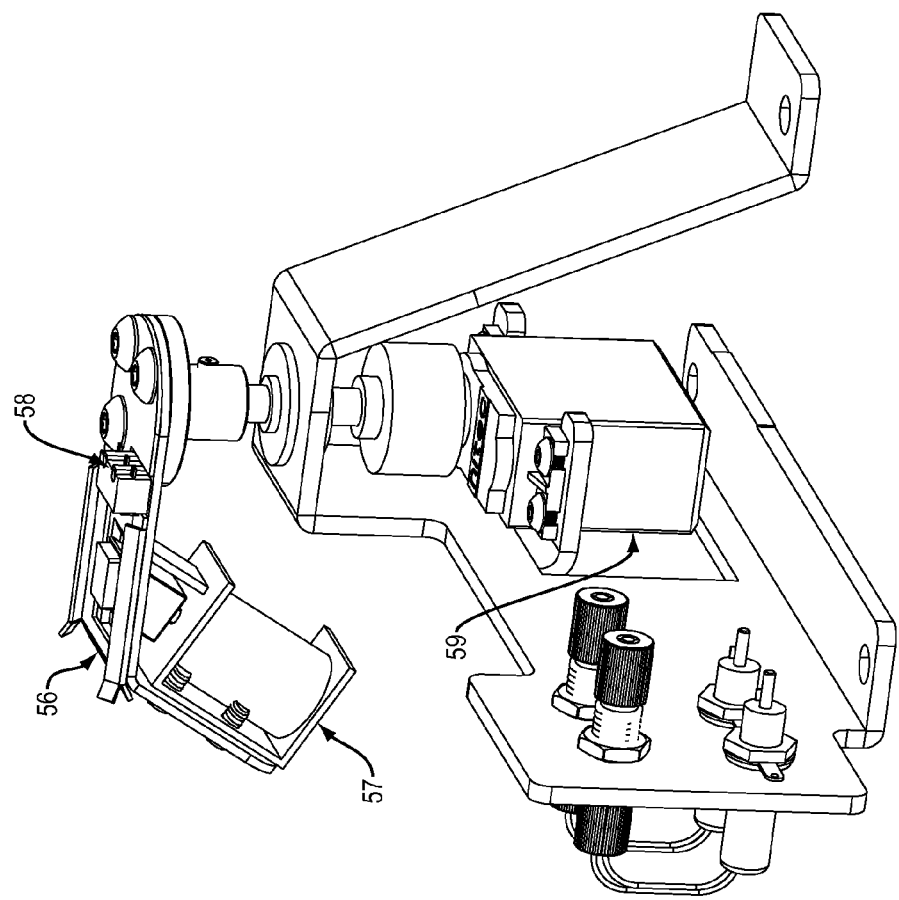

AUTOMATED MICROSCOPE FOR BLOOD CELL ANALYSIS

CROSS REFERENCE TO RELATED APPLICATIONS

Not Applicable

FEDERALLY SPONSORED RESEARCH

Not Applicable

SEQUENCE LISTING OR PROGRAM

Not Applicable

FIELD OF THE INVENTION

The invention relates to an apparatus for automatic microscopic analysis of stained blood cells. The invention employs means of motion in the X, Y and Z directions that is computer controlled, reproducible and low friction, coupled with software for focusing, finding an appropriate area on a blood smear in which to perform the test, finding cell candidates at low power within that area, capturing digital images of those cells at high power, counting the cells and grouping them according to their color, size and morphology. The base of the apparatus is a low cost polymer concrete material that is stable to temperature changes and is energy absorbent. Additionally, the apparatus is mounted upon polymeric shock absorbers. The apparatus is unreactive to ambient temperature changes and vibrations.

BACKGROUND OF INVENTION

Microscopic blood tests are among the most diagnostically important and most frequently ordered tests in hospital and clinical environments worldwide. These tests are critically important for the screening of patients and the monitoring of treatment progress. Typically to perform a differential white blood cell count, a technician fixes and stains a blood slide. The red blood cells stain red and the white blood cells stain blue. The technician then mounts the slide in a manual microscope. At low power (usually a 10× objective) the technician must move the microscope up and down (Z direction) to focus the microscope on the slide and move the stage (X and Y directions) to find the areas of interest; note those areas; change the objective to a medium level (usually a 40-50× objective), commonly by turning a turret; refocus and reposition on the area of interest in order to locate and examine one hundred white blood cells; change the objective yet again to still higher power (usually a 100× objective) and immerse the slide and microscope objective into a blob of oil. The technician must then relocate the areas of interest to search for cells with the color, size and morphology of interest. All this focusing and stage movement is usually done manually and takes a significant amount of time. Typically, a technician spends five to six minutes per slide to do all these procedures. Positional and alignment errors can be introduced during these manipulations. For the highest power lens immersing of the lens and slide in a blob of oil dirties the whole system by capturing dust and other ambient materials. The object lens must be cleaned with care to avoid scratching the surface. The oil also tends to migrate to other microscope parts as well as the immediate work area. Counting of cells is a mindless, tedious task, given to distraction and human error. In sum, present day manual methods are time consuming, tedious, costly and can lead to errors. Clearly there is a need for the automation of these tests, particularly in a high volume clinical situation. Moreover, in order to keep the long term costs manageable, such an automated system needs to be robust and require minimal maintenance.

Several automated systems for analysis of stained blood cells have been developed to perform many of these tasks. Unfortunately, these automated systems are built around conventional microscopes, which are not designed for extended use in high volume applications. Also focus, X-Y transport and objective lens mechanisms designed for manual use exhibit backlash effects making difficult reliable and reproducible positioning, which is necessary for high quality imaging operations. Additionally, the adaptations of conventional microscopes do not address the problems of ambient jarring and temperature changes, which can translate to large positional errors.

In view of the problems in the deficiencies in the current automated microscope systems for blood analysis, there is a need for an improved configuration of an automated, precise, computer aided microscope that is rapid, inexpensive and robust.

SUMMARY OF INVENTION

The present invention uses new approaches to create a novel automated blood cell analysis system. An exemplary embodiment of the present invention provides a much improved, low cost, computer controlled microscope system for this analysis of blood cells. This system allows the tedious parts of the blood analysis to be done unattended, allowing the technician to focus on interpretation of the results.

In one aspect, microscope slides with a blood smear and cover glass are further prepared by coating with a thin film of oil of about 20μ thickness, which provides high quality digital images under high powered magnification that are virtually indistinguishable from the results from the traditional immersion technique without all the attending messy problems of the oil blob.

In another aspect, microscope slides are introduced into the apparatus in a carousel. The slides are held in the carousel slots by carefully designed clips. These clips maintain the slides to within 0.25 mm of the slot center. Once in the carousel, the clips hold the slides in place sufficiently firmly that even if the carousel is turned upside down the slides will not fall out; yet they are readily removed either by a gripper mechanism or by the technician. The carousel may be completely or partially filled. The slides can be coded and the results archived with the patient records.

In yet another aspect, the use of computer controlled, linear induction motors that are indexed to an encoder strip affixed to a thermally stable, energy absorbing base allows rapid, low friction movement of the microscope stage in both the X and Y directions that is reproducible and precise to within 0.5μ. By indexing the linear motors to a calibrated encoder on the base, all motions of the stage are part of a closed loop system, eliminating any variations from ambient changes, such as temperature or jarring. The loop is closed in the sense that the linear motors are optically encoded and positional information is constantly fed back to the linear motor controller. The optical encoders are fixed relative to the base and the microscopes are fixed to the base as well. That base is rigid and dimensionally stable with regard to changes in temperature. The fact that both the motor/encoder subsystem and the microscopes are fixed to the same rigid base minimizes the effect of low-frequency ambient vibration.

In still another aspect of this invention, the traditional microscope with rotating turret is replaced with two single microscope objectives, which move together, each with its own camera and light source. The microscope subsystem is located on a tower, which is a vertical extension of the base. These improvements eliminate any potential alignment errors that may be caused by turret rotation.

In yet another aspect, voice coil technology, under computer control, is used to focus the microscopes without any mechanical gearing, such as an elevating screw. The voice coil consists of a coil and a magnet. The coil is affixed to the microscope tower and the magnet is attached to the objective carriage. As current flows through the voice coil, the magnet and the objective carriage move in response. The objective carriage is attached to the tower by springs to keep the assembly under positive tension. Additionally a linear cross roller bearing is attached to the objective carriage to limit movement to the Z direction. Like in the X and Y directions, the motion in the Z direction is also controlled with indexing in increments smaller than what are commanded by the host software. In total, this allows rapid, low friction, precise positioning to within 15-20 nm. This results in high quality digital images for analysis.

In another aspect, there is a gripper mechanism to acquire a microscope slide by its longitudinal edges and transport the slide to the microscopes. The gripper is made up of two arms or furcations, one of which is pinned pivotally at two points to a cam controlled by a servo motor. The turning of the cam opens and closes the gripper. The arms of the gripper are bridged by a spring, ensuring that the slide is positively grasped as a default mode. One of the arms has free play of about 0.05 inches to accommodate microscope slides of differing width. The gripper is mounted on top of the linear motor assembly. In effect, the microscope slide in the gripper constitutes a stage for the microscope.

In another aspect, the use of an optical target as a fixed focal point on the slide gripper allows calibration of the stage vis-à-vis the microscope objective to be done in a relative manner. This too minimizes variations introduced by ambient factors, such as outside vibrations and temperature changes.

Another aspect of the invention is a method of computer controlled counting of the white blood cells, image analysis of the color, size and morphology of the cells and a preclassification grouping according to cell type, allowing the technician to concentrate on the analysis of the blood sample. The preclassification information can be reviewed and verified by the user and then downloaded to a central file for archiving with the patient history.

In a further aspect, the apparatus has a STAT mode, which allows a single emergency slide to be put in the queue ahead of any samples loaded in the carousel waiting to be run. When a slide is placed in the STAT access slot a switch is activated which triggers a servo motor to move the slide into the apparatus by turning the slide approximately 180° to be in position for slide pick-up by the gripper. The system responds to the switch activation by giving this slide priority over those waiting in the carousel. This insures the flexibility necessary in a hospital environment, which often has urgent situations.

The invention facilitates accurate, low cost, capture, analysis and archiving of digital images of blood cells. The invention, however, is not limited to differential white blood cell analysis. With the appropriate software it is possible to analyze other biological specimens. As an example, this invention can be programmed to search a slide for just a few specially stained cells among hundreds of thousands of cells. This would be particularly useful in probing for rare event cancer cells both prior and subsequent to chemotherapy.

The principal objective of the present invention is to provide an inexpensive apparatus, which can rapidly produce high quality, archivable digital images of blood cells and pre-classify them, resulting in a substantial saving in technician time. In addition to saving labor this automated system of differential white blood cell analysis eliminates the tedium of manual review and thereby many of the potential error sources. Automated performance of this monotonous task frees the technicians to do what they do best and use their valuable time on the decision making process.

Yet another objective is to provide an apparatus that is affordable. Moreover, the apparatus can be updated quickly and inexpensively to an even higher level apparatus with future improvements in software.

These and other features and advantages may be better understood by reading the following detailed description, with appropriate reference to the accompanying drawings

BRIEF DESCRIPTION OF DRAWINGS

Exemplary embodiments of the invention are described herein with reference to the drawings. It will be understood that the particular apparatus embodying the invention is for the purpose of illustration only and not as a limitation of the invention. Referring now to the figures:

FIG. 9 is a view of the STAT Access Assembly.

DETAILED DESCRIPTION OF INVENTION
(PREFERRED EMBODIMENT)

Figure 2A:
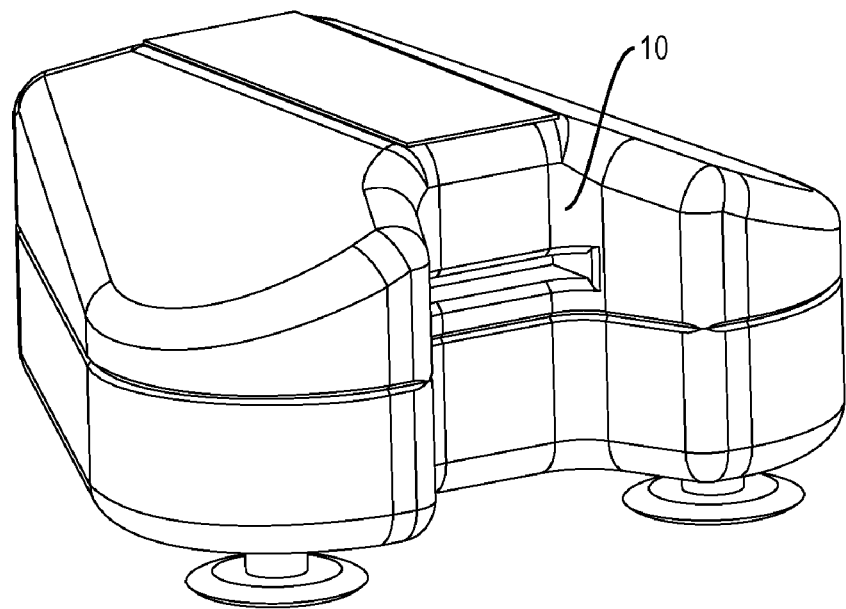
FIG. 2A is a view of the oiling device and FIG. 2B is a side cutaway view of the oiling device.
Figure 2B:
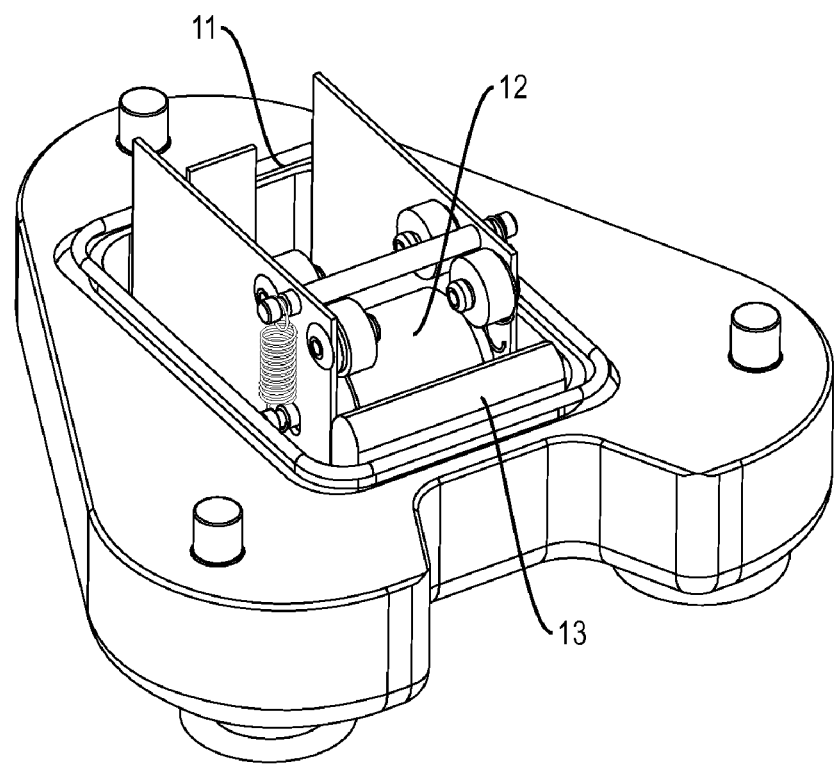

FIG. 2, the oiling device 5 consists of a slot 10 for access, a well 11 containing microscope immersion oil, an applicator 12 to coat the slide and a wiper 13 to remove excess oil.

Figure 1:
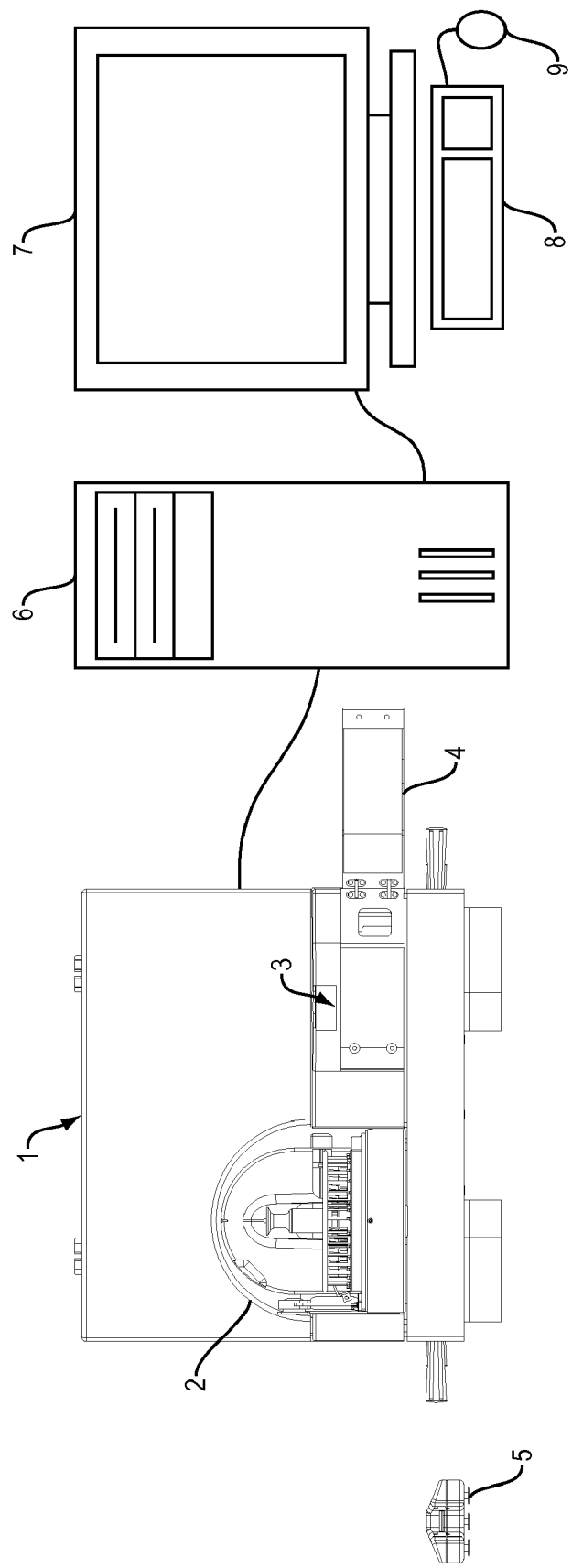
FIG. 1 is a view of the Easy Cell System.

FIG. 1, the apparatus comprises a computer controlled microscope subsystem incorporated in a housing 1. The microscope subsystem communicates with the computer 6 via a cable connected to USB ports on each. The housing has portals for a slide carousel 14, a slot 3 for STAT samples and an access panel 4. A computer subsystem comprises a computer 6 with a monitor 7 and other peripherals for storage, display and user input, such as a keyboard 8 and mouse 9.

Figure 5:
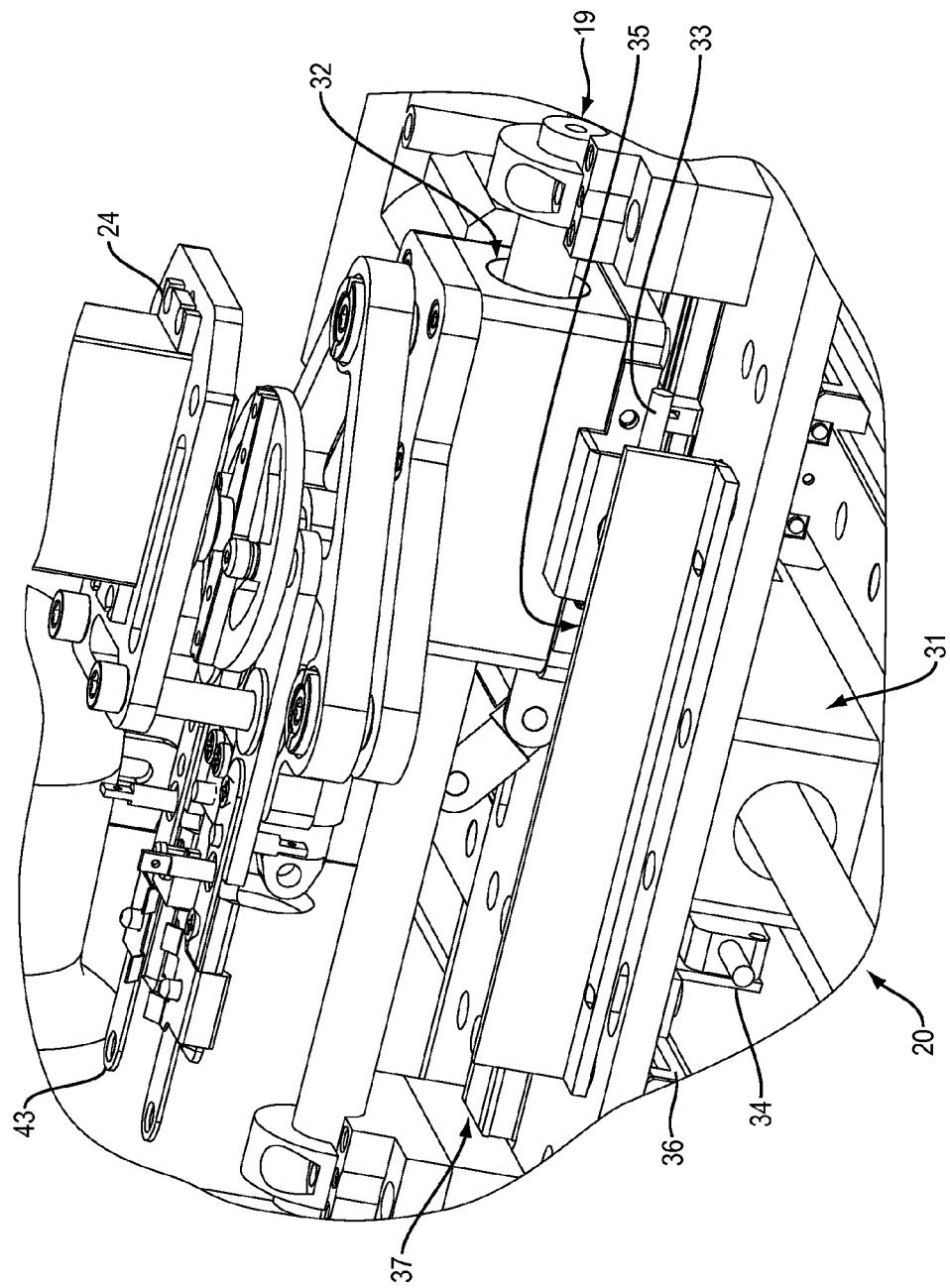
FIG. 5 is a view of the X-Y carriage.

FIG. 5, the microscope subsystem has computer controlled, linear induction motors for movement in both the X 31 and Y 32 directions. The X-direction motor 31 travels along a center rail 20 and two linear bearings 21. The Y-direction motor 32 also travels along a center rail 19 and one linear bearing 37, attached to the X-direction motor. The linear motors 31 and 32 are optically indexed 35 and 36 to the base 23 via calibrated encoders 33 and 34 and act as a carriage 17 for the transportation of the microscope slides.

Figure 10B:
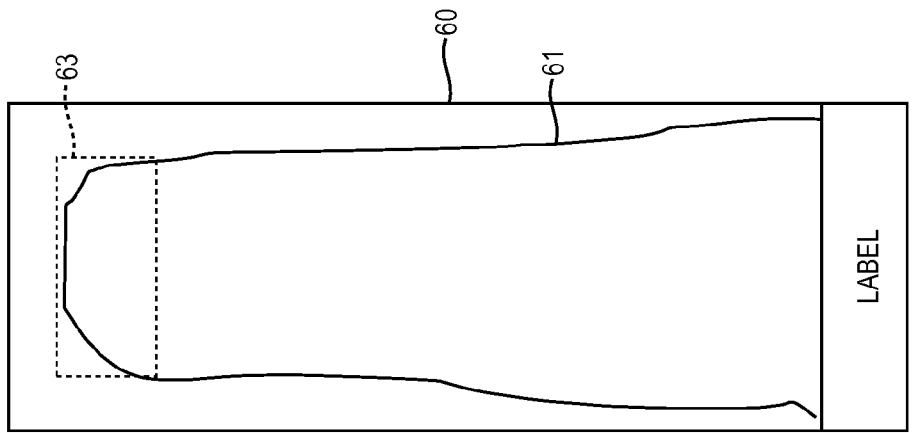
FIG. 10A is a microscope slide with a blood smear and a hypothetical diamond and FIG. 10B is microscope slide with blood smear and hypothetical rectangle.
Figure 10A:
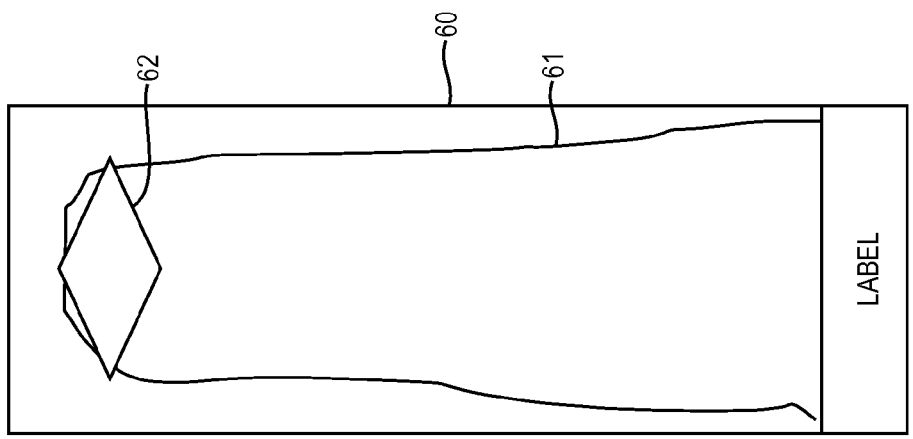

FIG. 5, attached to the Y-motor 32 is a gripper 24 for acquiring a microscope slide by its longitudinal edges from the carousel 14 (FIG. 3) or from the STAT entry 3 (FIG. 1). Mounting the gripper 24 (FIG. 5) on the linear induction motor 32 and sufficiently extending the range of the linear induction motor 32 allows it to be used for transporting slides to and from the carousel. The gripper 24, together with the microscope slide 60 (FIG. 10), acts as the microscope stage. This eliminates any need for additional slide transfers within the system. The gripper arms 38 and 39 (FIG. 6) are opened and closed by a servo motor 40 attached to a cam 41. The gripper arms 38 and 40 are bridged by a spring 42 to maintain the closed position as the default. This gripper means 24 has an optical target 43 (FIG. 6B) attached as a fixed focus point for calibration of the gripper means 24 relative to the microscope subsystem.

Figure 7B:
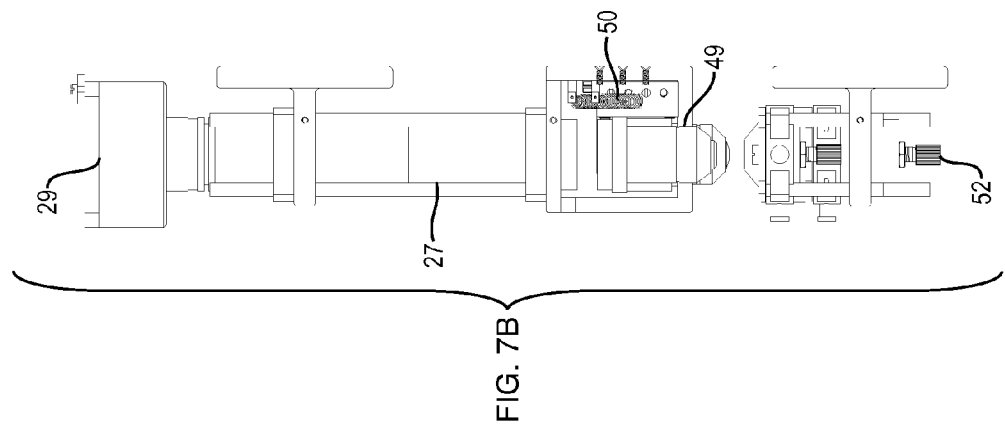
FIG. 7A is a view of the Microscope Sub Assembly and FIG. 7B is a side view of the High Powered Microscope.
Figure 7A:
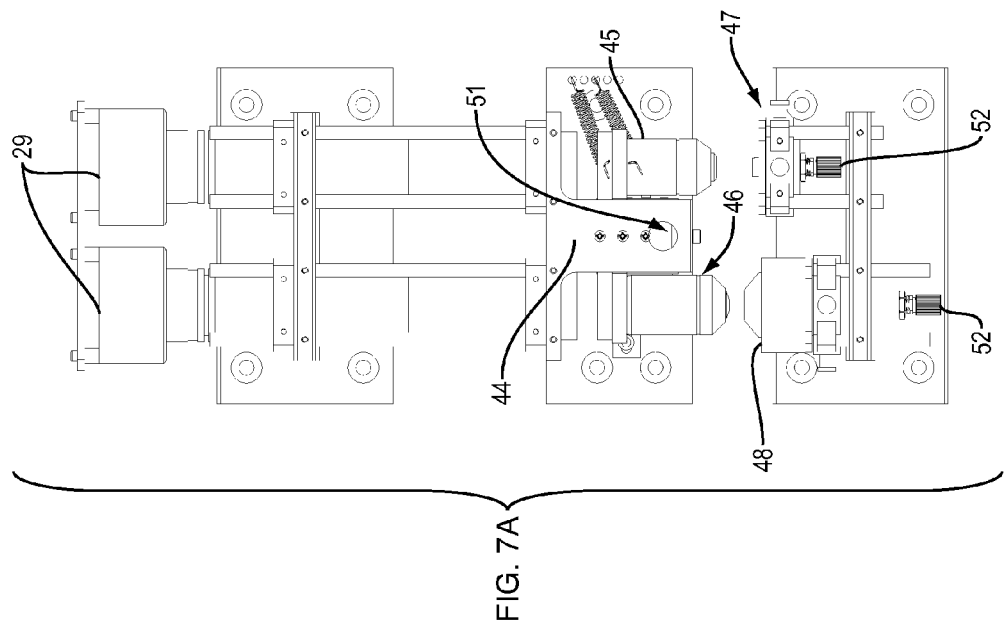

FIG. 7, the microscope subsystem includes two microscopes 26 and 27 on a tower 28. The microscopes are in two parts. The upper part is fixed to the tower 28. The lower part consists of the objective carriage 44 and objectives 45 and 46 and is stabilized by a linear cross bearing 51. At the top of each microscope there are digital cameras 29 to capture images from the microscope slide. In addition to the microscope cameras, there is an additional camera/barcode reader 30, which captures an image of an identifier on the end of the microscope slide 60 (FIG. 10) and/or scans a bar code, if one is present. This microscope subsystem (FIG. 7) is positioned in the Z direction with a computer controlled voice coil 49, under positive tension from two extension springs 50, which is indexed to the Z direction to within 15-20 nm. The coil portion of the voice coil 49 is attached to the optics tower 28 and the magnetic portion is affixed to the objective carriage 44.

Figure 8:
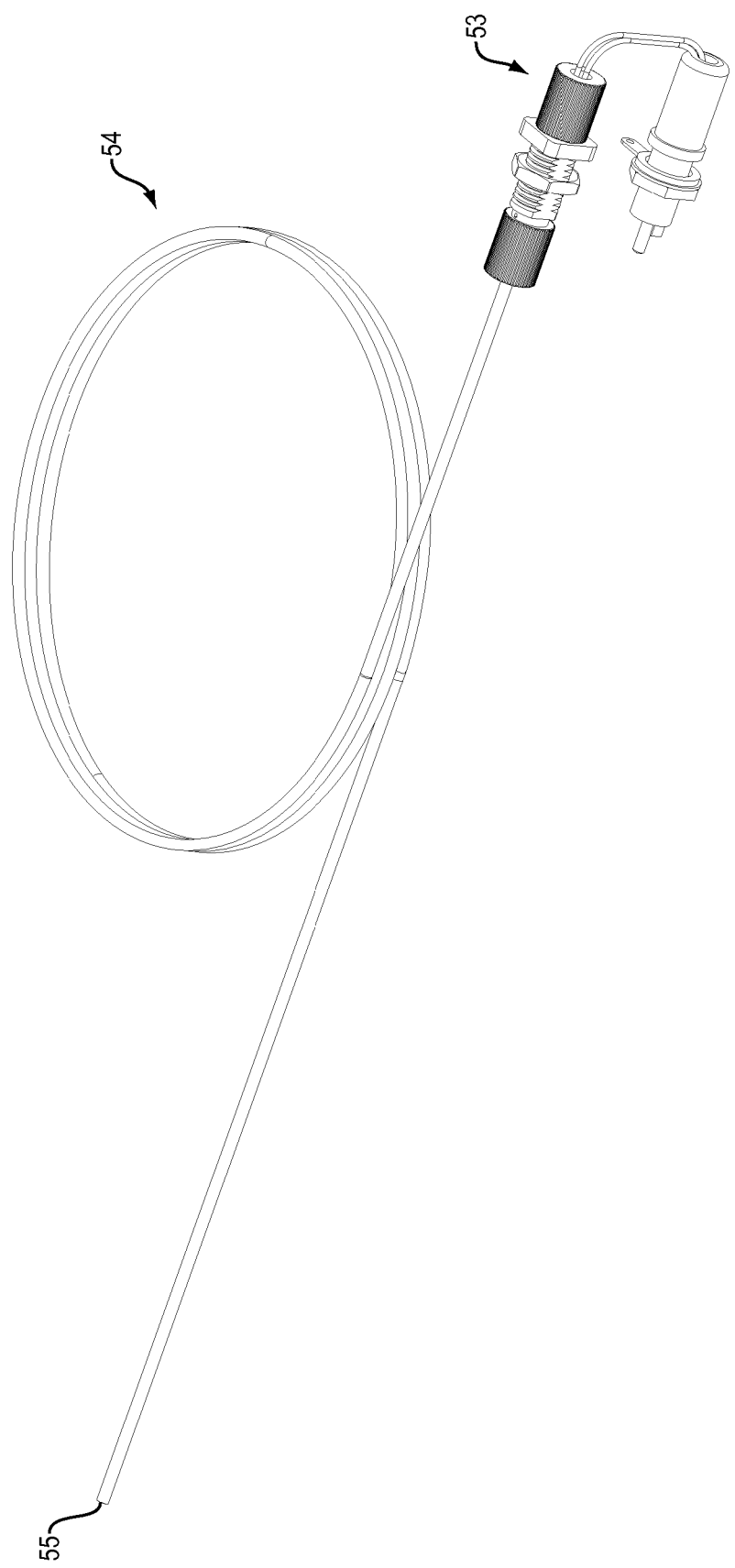
FIG. 8 is the LED light source and the conducting fiber optics.

FIG. 8, light for the microscope is obtained from LED sources. Light from the LED 53 is conducted by coiled fiber optics 54 to below each microscope to illuminate the slide while it is under the microscope. The optical fiber is coiled to make the light isotropic and eliminate a central hotspot. Each microscope has a light condenser 45 and 46 (FIG. 7) below the stage to collimate the light. The 100× objective 46, because of its minute field has a more finely focused light condenser 48.

The purpose of the system is the unattended computer controlled scanning and analysis of blood smears 61, prepared and stained on a microscope slide 60 (FIG. 10). The system scans for the optimum area of examination; locates the white blood cells of interest; acquires a digital image; counts the white blood cells as the images are acquired; preclassifies the objects according to known color, size and morphology; archives the images and displays them for operator verification and analysis.

Figure 3:
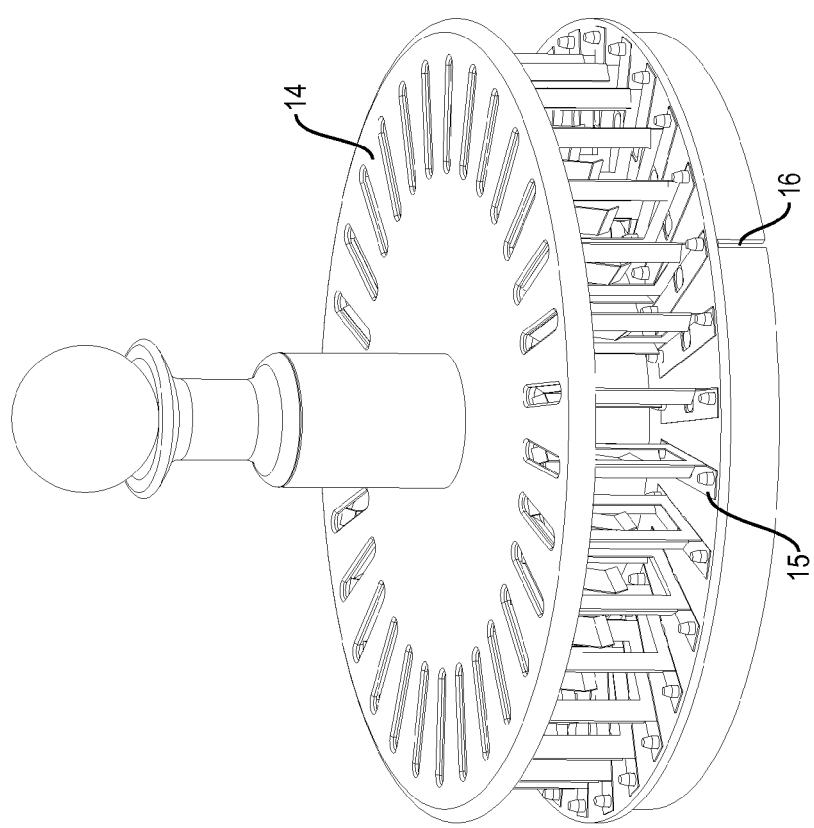
FIG. 3 is a view of the Carousel.
Figure 11:
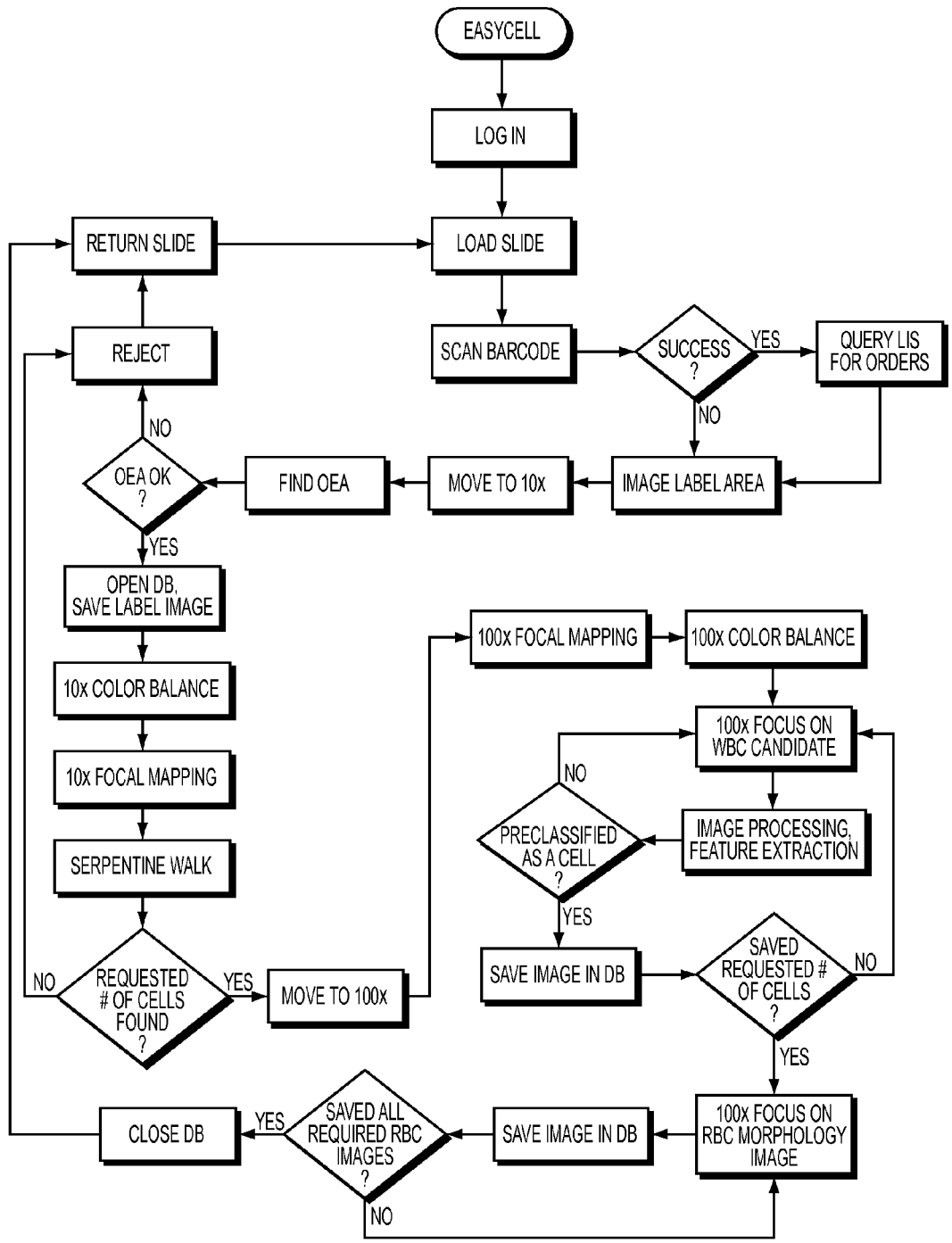
FIG. 11 is a Flow Chart of the Overall Process.
Figure 12:
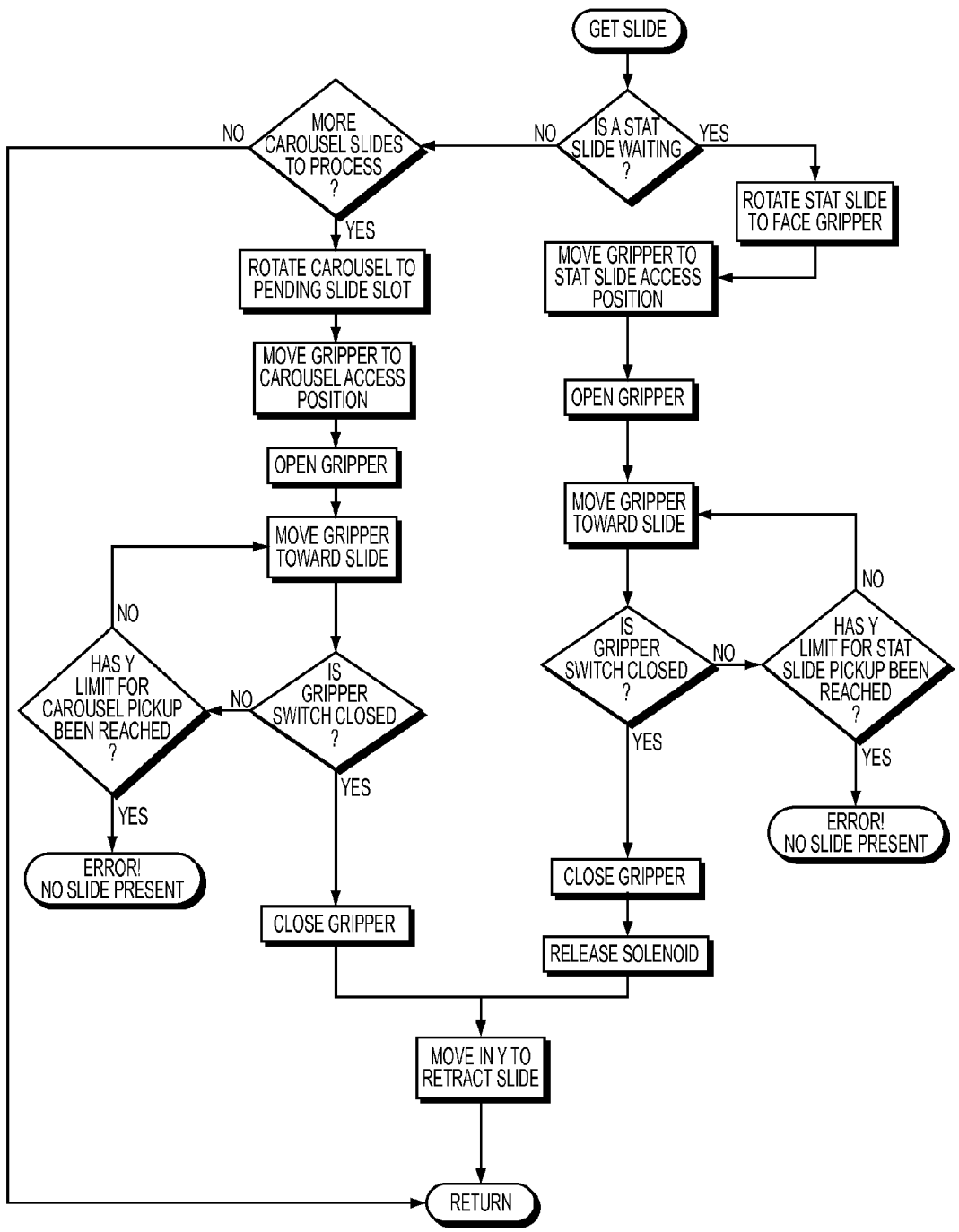
FIG. 12 is a Flow Chart for the process of retrieving a slide

As an overall study (FIG. 11), during operation of the system first a microscope slide, with stained blood smear and topped with a cover slide, with the cover slide down, is inserted into the oiling device 5 through slot 10 (FIG. 2). The slide is pushed across the applicator, the lower potion of which is immersed into the well 11. This coats the microscope slide with immersion oil. As the microscope slide is extracted from the oiling device 5, excess oil is removed by a wiper 13. The microscope slide is now ready for insertion into the carousel 14 (FIG. 3). Each carousel 14 holds up to 30 prepared slides. When the operator starts the sequence (FIG. 12), the carousel 14 (FIG. 3) is rotated and examined as to which slots are occupied. Then a microscope slide 60 (FIG. 10) is removed from the carousel 14 by the gripper 24 (FIG. 6), using the microscope slide's longitudinal edges. Alternatively, if a slide 60 is placed in the STAT access slot 3 (FIG. 1), a trip switch 58 (FIG. 9) indicates the presence of the slide 60. That slide will then take priority over other slide in the queue. Slides are returned to their original positions after examination.

Figure 4:
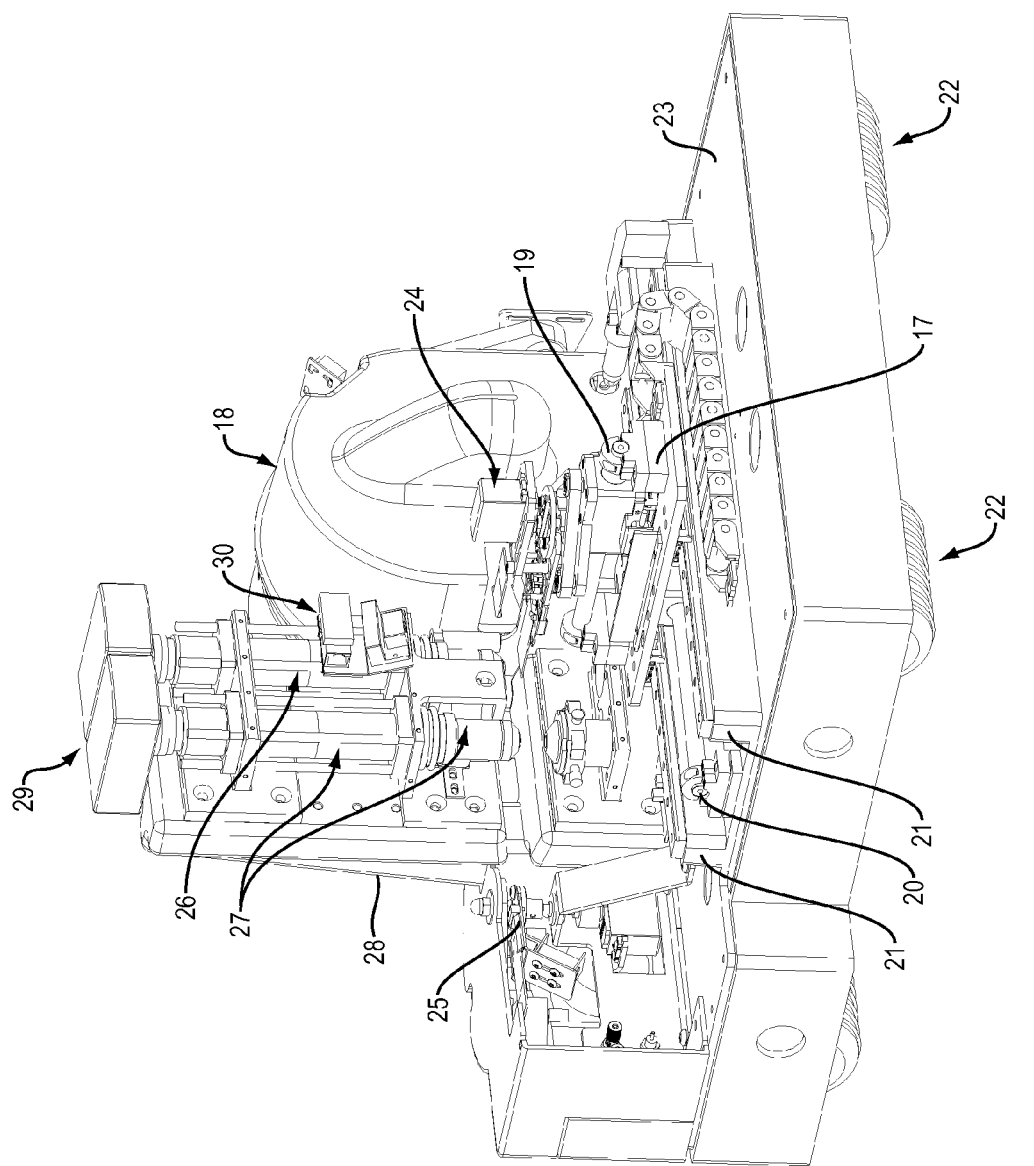
FIG. 4 is a view of the Easy Cell Apparatus with the housing removed.
Figure 13:
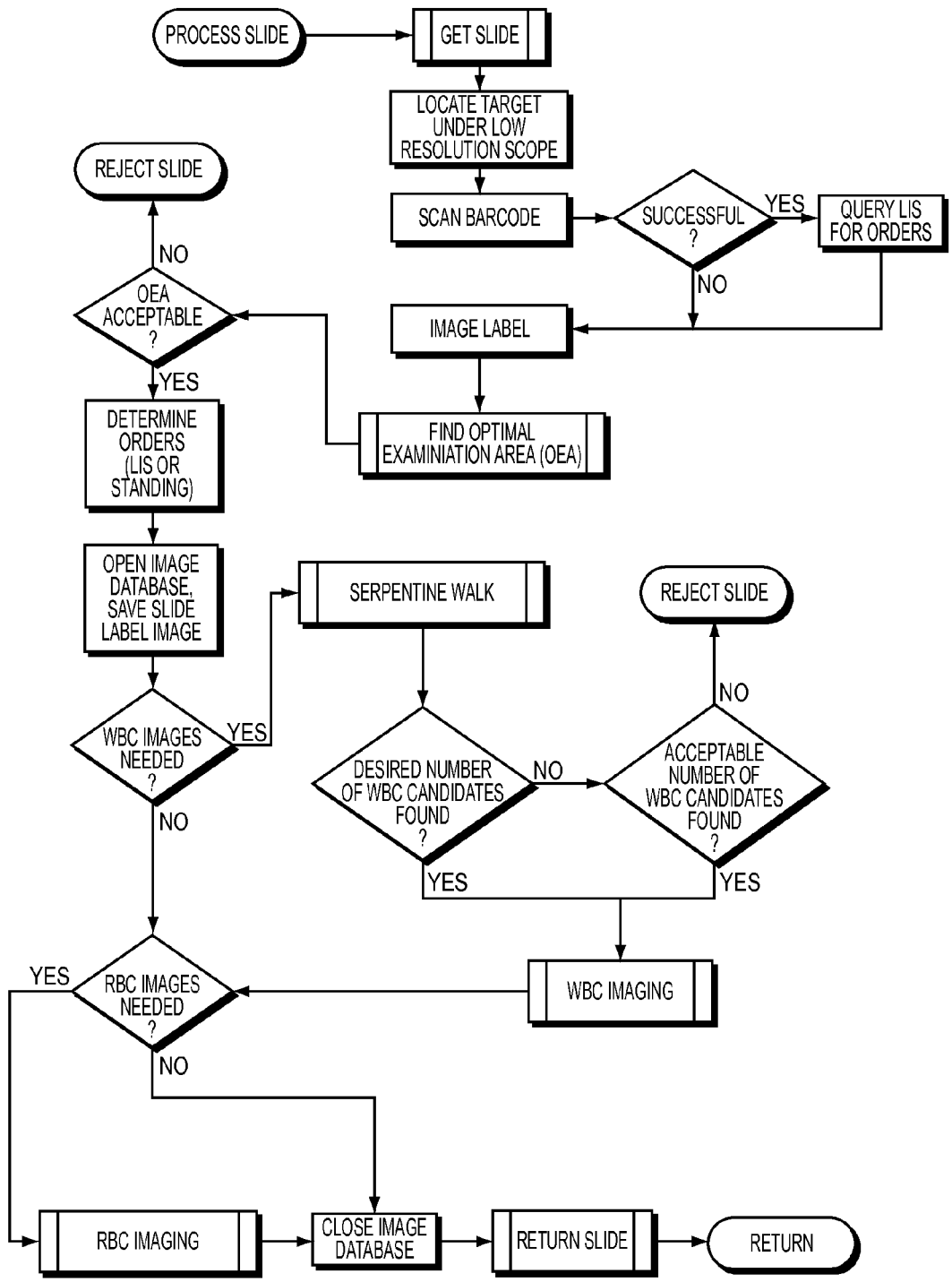
FIG. 13 is a Flow Chart for processing the retrieved slide.

FIG. 13, the slide is then moved by the X-Y carriage to the microscope tower 28 (FIG. 4). As with all slides, either from the carousel 14 or the STAT slot 3 (FIG. 1), the identifying mark at the end of the slide is scanned by the camera/bar code reader 30 (FIG. 4). If the mark is a bar code, it is interpreted and becomes the identifier for that slide. If not, a digital image is taken of the slide end for identification purposes. The digital image is then stored with the slide information.

Figure 6A:
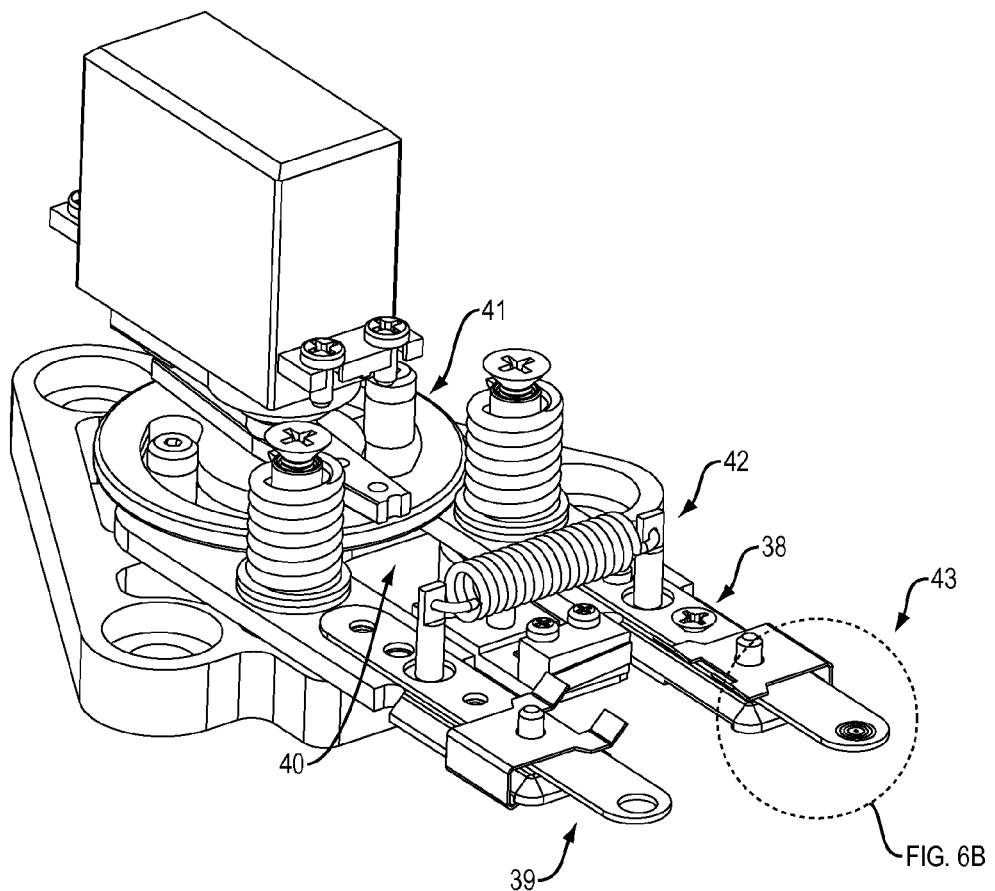
FIG. 6A is an over head view of the Gripper Device and FIG. 6B is the Fixed Optical Target
Figure 14:
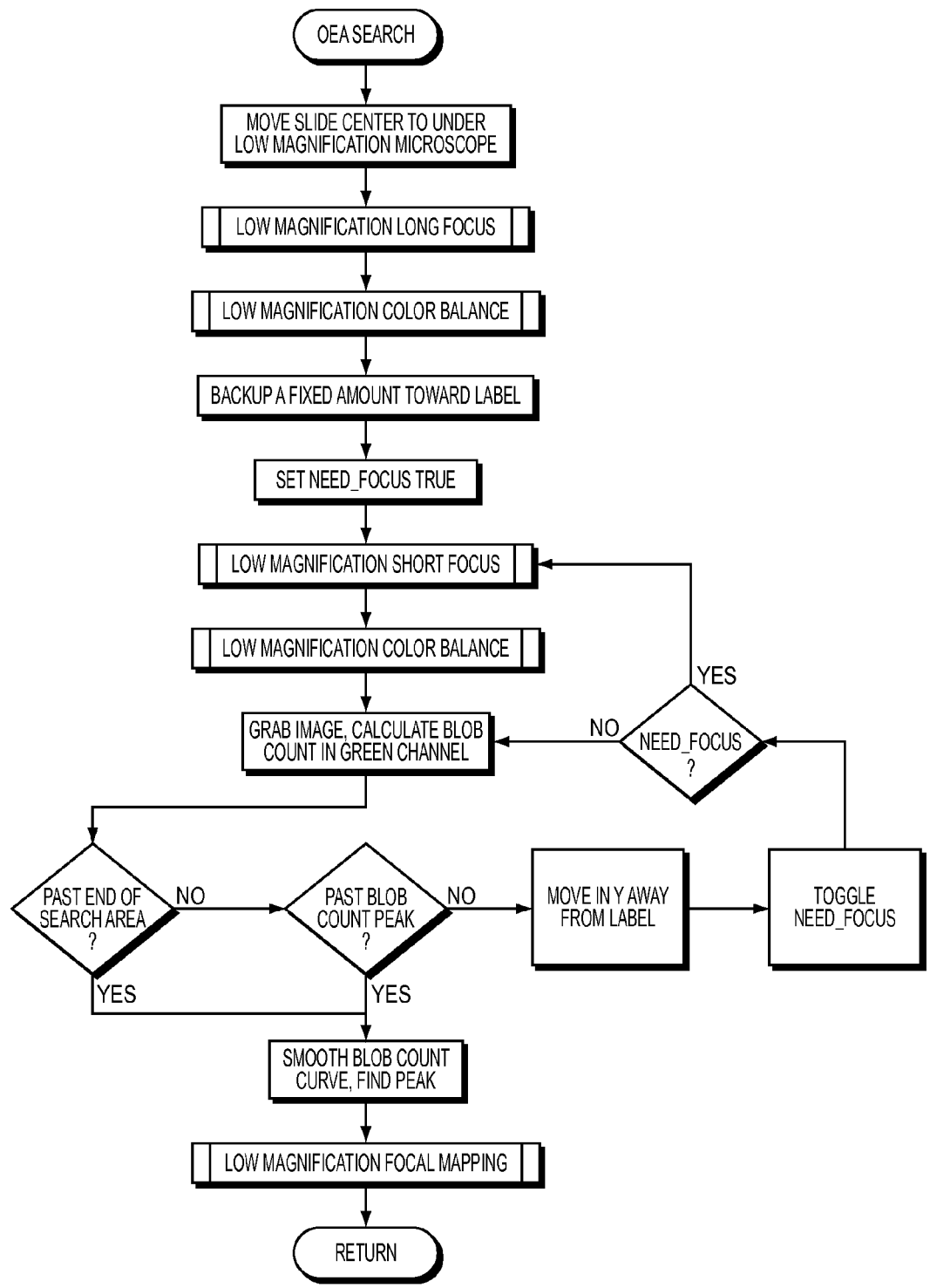
FIG. 14 is a Flow Chart for determining the Optimal Examination Area.

The slide is placed under the lower resolution microscope 26 (FIG. 7), typically fitted with a 10× objective. The relative focus is determined from the fixed optical target 43 on the gripper arm 38 (FIG. 6). FIG. 14, the optimal area of examination is determined preferably by sweeping the longitudinal center of the slide from near the label and continuing to the end of the smear 61 (FIG. 10). The number of red blood cell objects in each field is counted. A curve of red blood cell count is created by examining each successive field. The optimal area of examination is assumed to be the region surrounding the peak of the curve. The peak of this curve is the starting point for slide examination. In practice, the red blood count rises steadily until the peak is found and then drops off quickly. This tends to put the Optimal Examination Area toward the end of the smear 61 (FIG. 10) rather than near the label end.

There are a number of well known methods and variations of determining focus. Simply put, focus is determined by edge contrast. In an unfocused image, color is evenly distributed across the image with little or no contrast between one area and another. As focus improves areas of differing color intensity become visible, but the edges are not sharp. At the focal point there is a distinct change with the images having crisp edges and maximal differences in color contrast. When the edge contrast of the object at those points is maximized, that is considered the focal point.

Figure 6B:
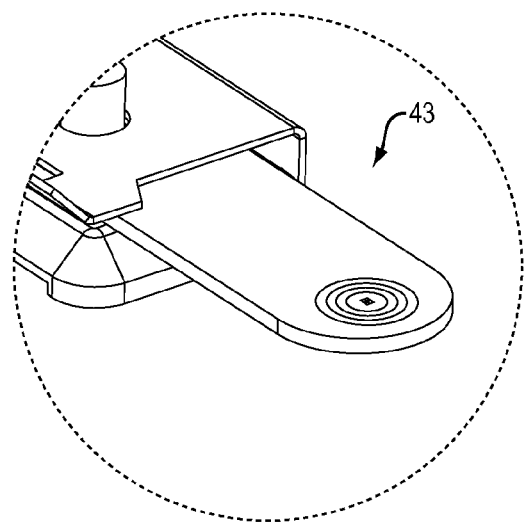
Figure 15:
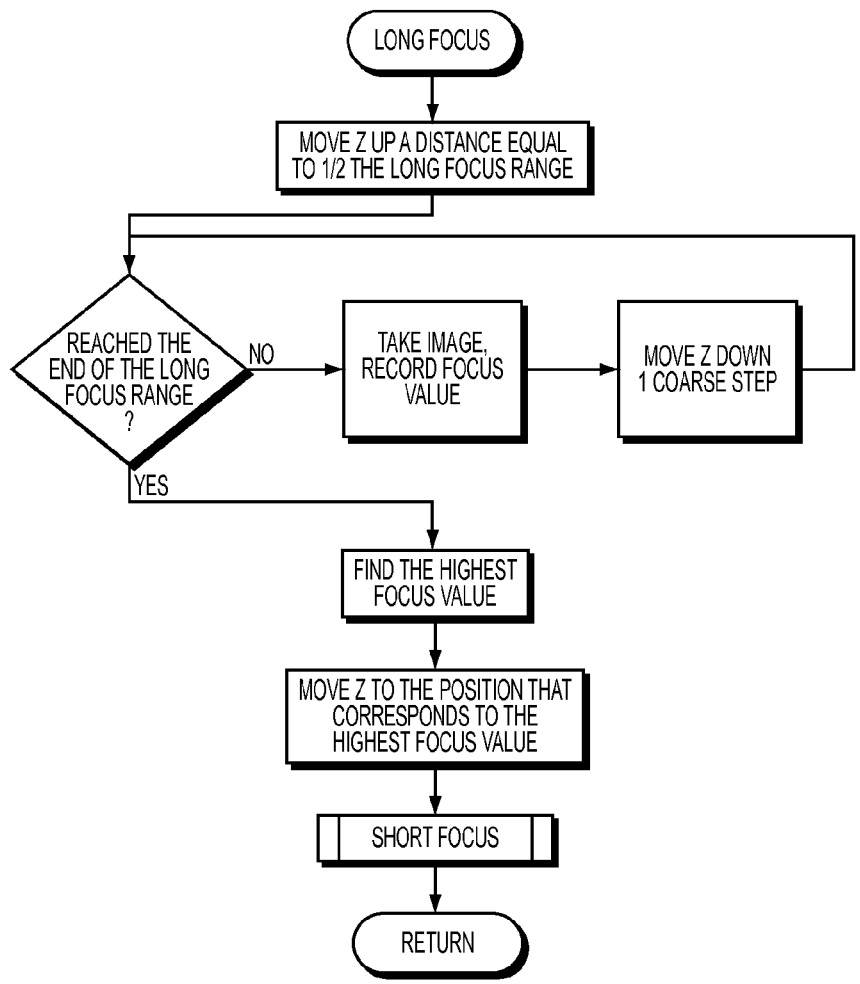
FIG. 15 is a Flow Chart for the Long Focus Operation.
Figure 16:
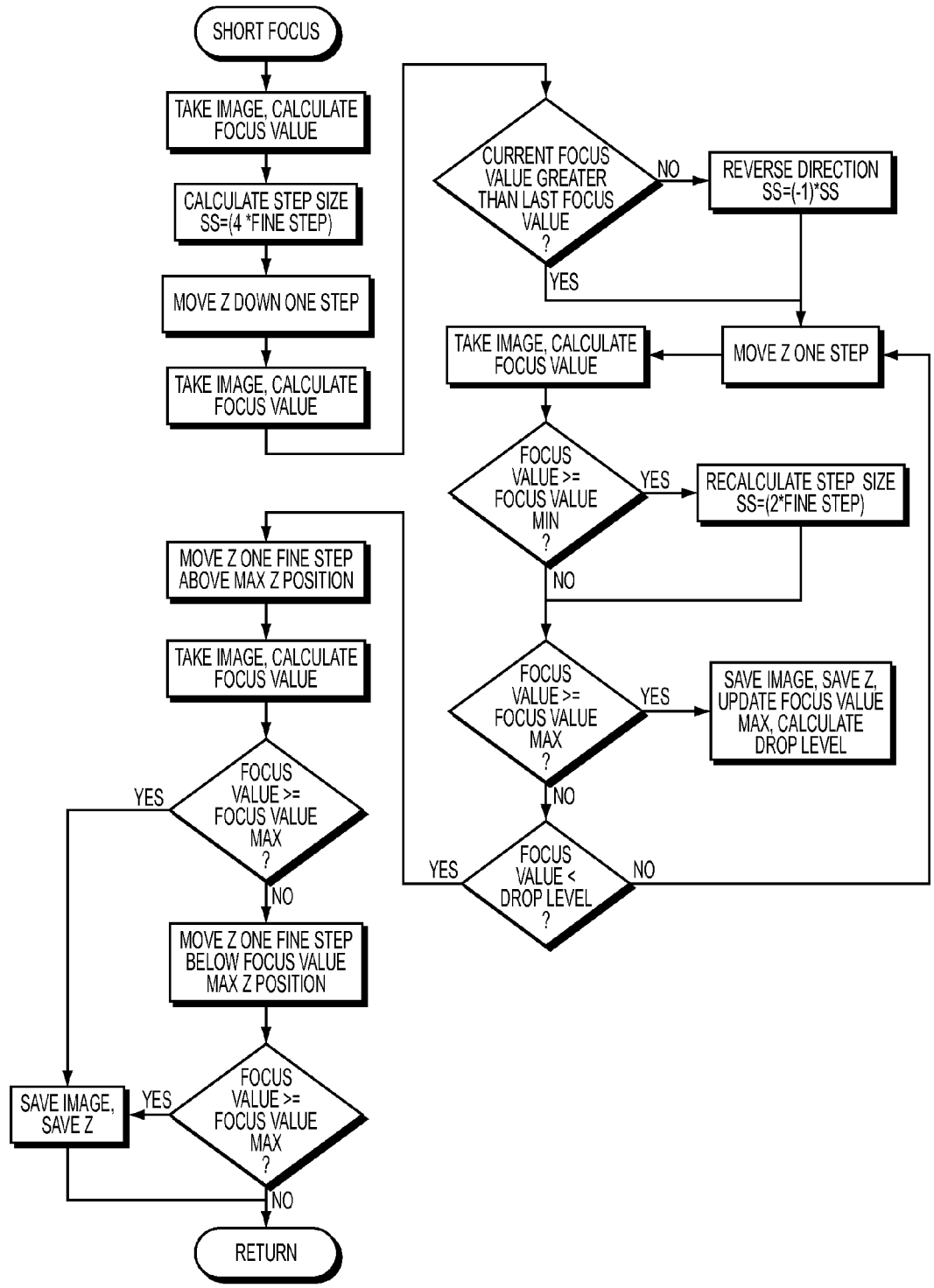
FIG. 16 is a Flow Chart for the Short Focus Operation.

There are two different focus operations to find that point of contrast. The first one is referred to as a long focus operation, FIG. 15. It is used when the approximate position of the focal direction is not known. The second operation is the short focus, FIG. 16, and is used when the approximate positions of the focal plane is known. Both operations are accomplished by stepping the microscope in minute distances from the fixed optical target 43 (FIG. 6B). The operations differ primarily in the distance along the Z axis that is searched for the focal plane and the amount of time spent on that operation. When the approximate focal plane is not known, more of the Z axis must be searched, which takes more time.

Figure 17:
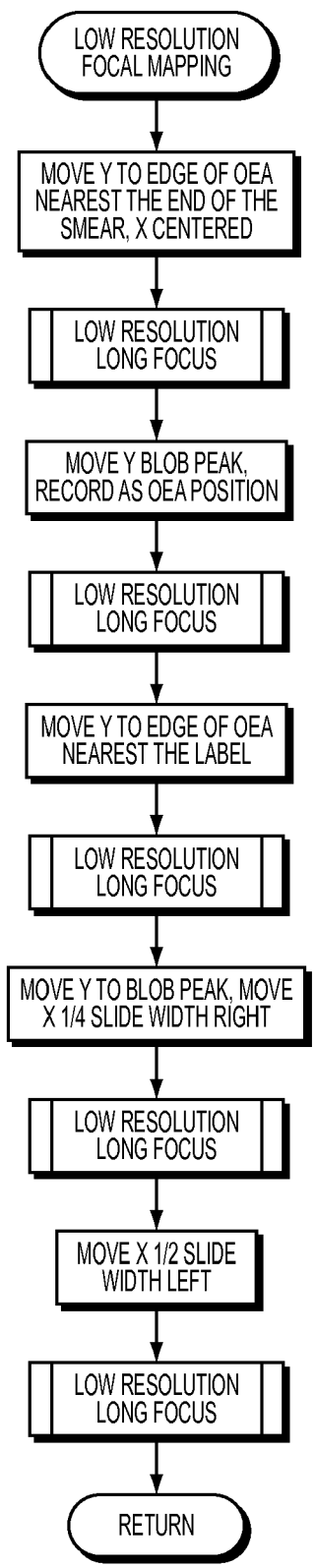
FIG. 17 is a Flow Chart for the Low Resolution Focus Mapping.

To determine the focus for each object of interest individually would be a time consuming process. In order to save time, a long focus operation is performed at a small number of positions and a focal plane map of the area of interest is computed, FIG. 17.

For the low power objective a focal plane map of the optimal examination area is determined by creating a hypothetical diamond shape 62 (FIG. 10A), relative to the rectangular shape of the slide. The first pair of diamond vertices is positioned along a line, which is perpendicular to the longitudinal edges and intersects the peak of the red blood cell count curve. The location of the vertices is offset from the edges one quarter of the width of the slide. The second pair of points is sited along the long axis of the slide that includes the peak of the red blood cell count curve and is located at the edges of the optimal examination area. Long focus operations (FIG. 15) are first performed on the latter pair of points together with the peak of red blood cell count curve.

Long focus operations (FIG. 15) are also performed on the remaining two diamond vertices. At each of these focal points the x, y and z values are noted. Once complete, the focal map can be used to compute the needed z value to produce a focused image for any given (x, y) point. It does this by computing the linear change in z along each x and y axis relative to the given point, then combining the two results to determine the final z value. From here only a short focus operation (FIG. 16) need be done.

Figure 18:
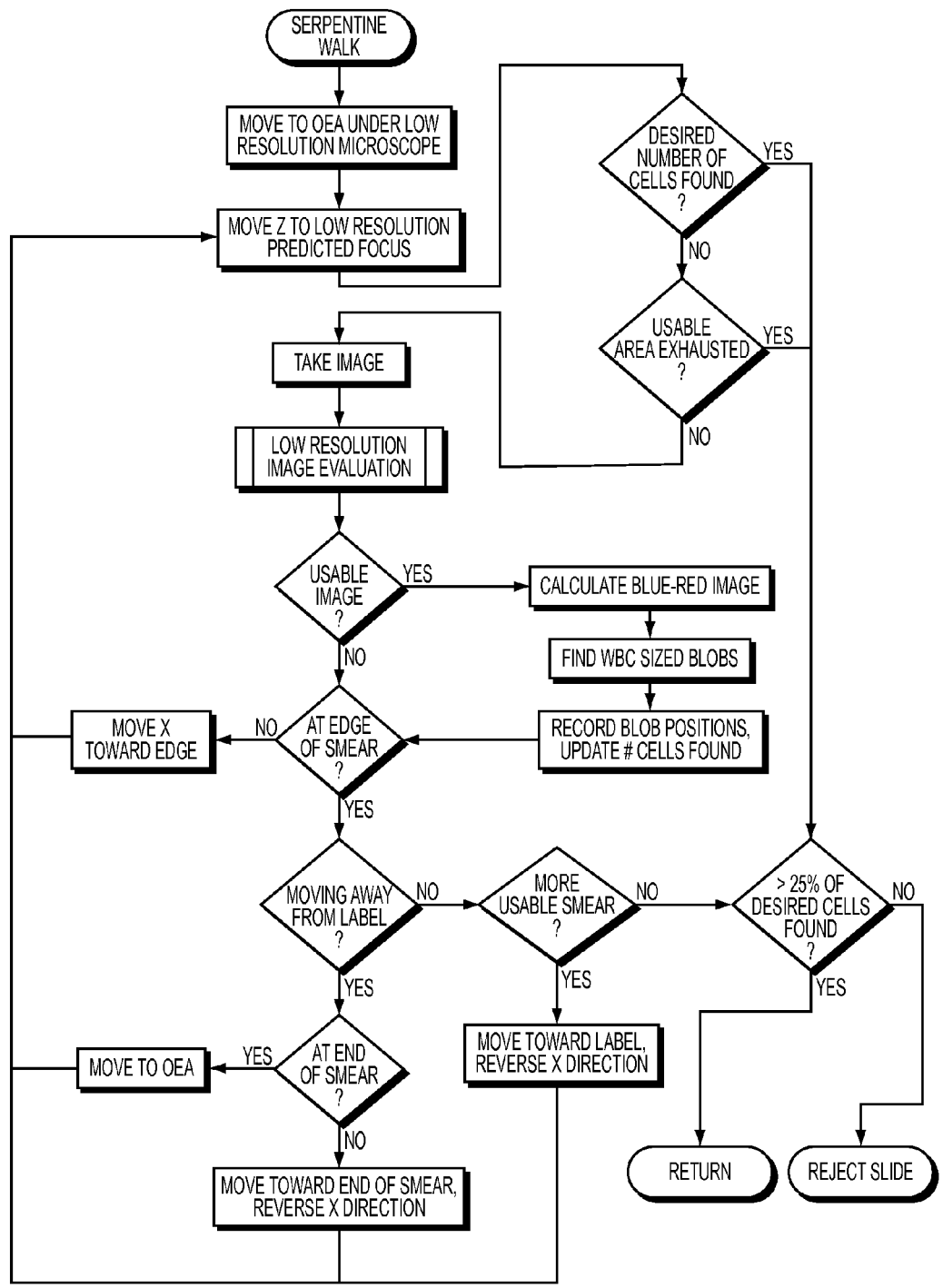
FIG. 18 is a Flow Chart for the Serpentine Walk.

Following the Focal Plane Mapping operation, the slide is moved under the microscope to search the Optimal Examination Area for appropriate fields from which white blood cell candidates may be taken. The peak of red blood cell count is used as the starting point and the slide is examined in a serpentine manner (FIG. 18). Use of the focal map provides the location of the focal plane for each field, so that no focus operations are required during this part of the procedure.

The clinical standard is to find white blood cells in areas of the smear where the blood cells are evenly dispersed. Because red blood cells are significantly more numerous than the white blood cells, it is an easier task to track the red blood cells for areas of even distribution, particularly under low power objective (10×). Each successive 10× field is examined for cell sized blobs.

Figure 19:
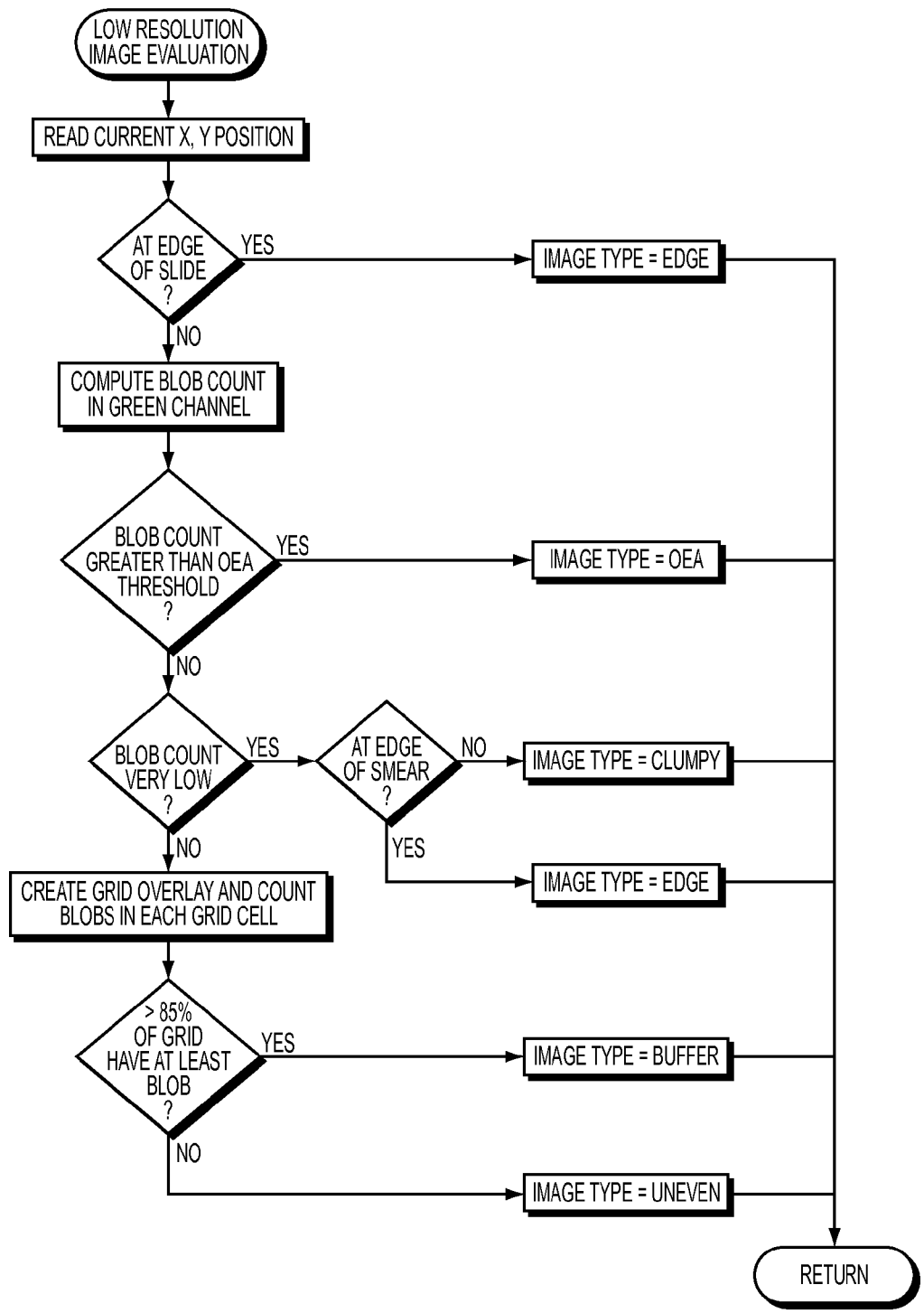
FIG. 19 is a Flow Chart for the Low Resolution Image Evaluation.

FIG. 19, from surveys of hematologists, it was determined that a field with at least 200 red blood cells is acceptable and a field with less than 140 red blood cells was unacceptable. If the count of cell sized blobs is above the larger threshold, the field is judged appropriate. If the field is below the lower threshold, the field is rejected. If the count is between these two demarcations, the largest blob in the field is noted. If this blob is larger than the largest known red blood cell, the field is rejected as having the cells too closely packed. Otherwise the field is considered usable.

When a field is evaluated as appropriate, the image is processed to subtract out signals from the background and red blood cells (FIG. 19). Areas of the field that are bluer than their environment are interpreted to be white blood cell candidates. The locations of the white blood cell candidates are computed and listed for later examination under the 100× objective. The serpentine search is continued until the required number of white blood cell candidates is identified or the Optimal Examination Area is exhausted.

Figure 20:
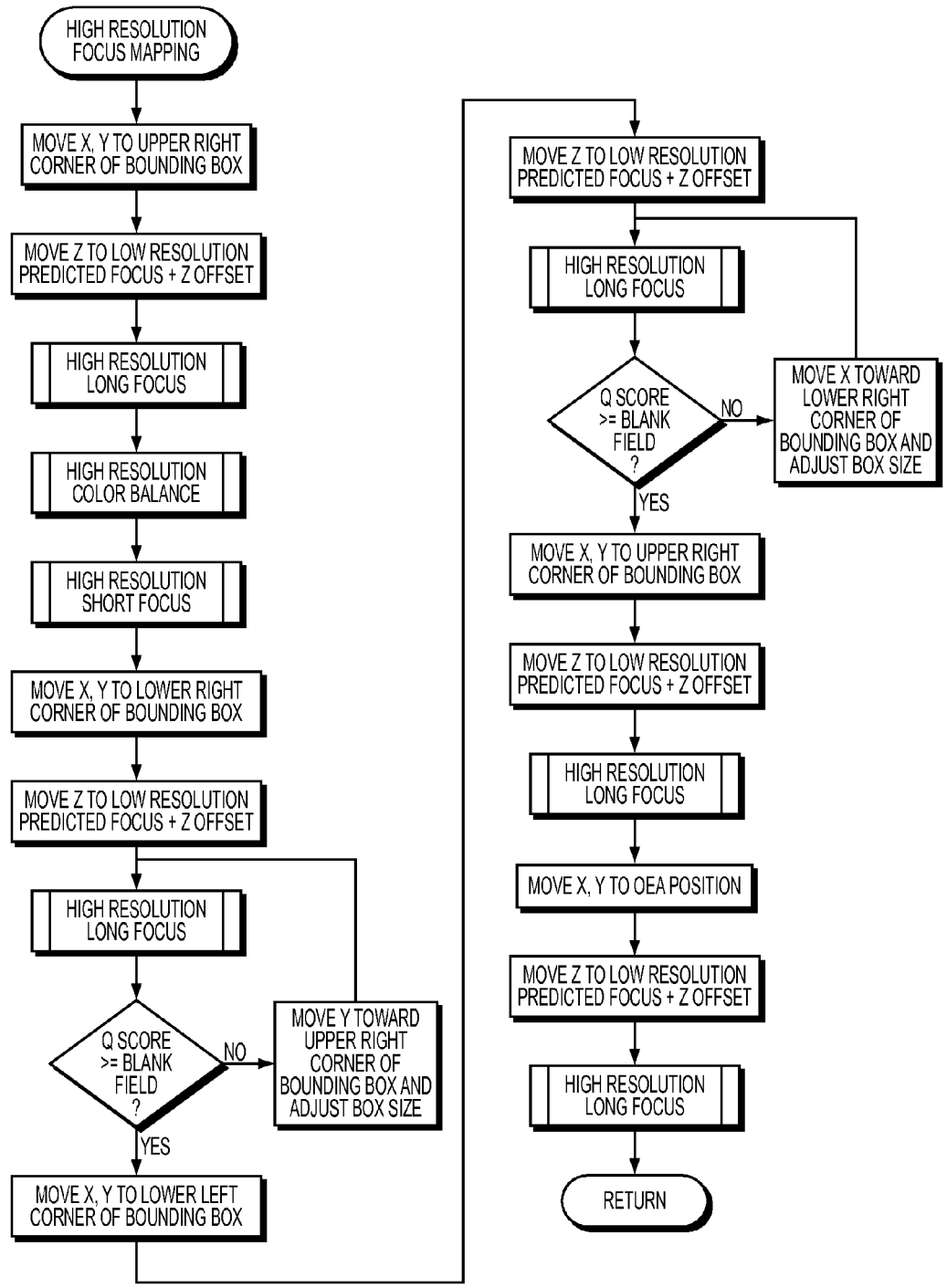
FIG. 20 is a Flow Chart for High Resolution Focus Mapping.

FIG. 20, after the low resolution scanning is complete, the slide is moved under the higher powered microscope 46 (FIG. 7). Because, planarity is less obvious under the significantly higher magnification, a new focal plane map needs to be computed. First the relative focus is determined from the fixed optical target. Then from the list of white blood cell candidate positions a hypothetical rectangle 63 (FIG. 10B) is created that encompasses all the white blood cell candidates. A long focus operation is performed at the lower (label end of the slide) left corner of the rectangle 63. A color balancing operation is conducted; followed by a short focus operation to see if a sharper focal peak has been created.

The slide is moved so that the upper left corner of the hypothetical rectangle 63 (FIG. 10B) is under the microscope objective. A long focus operation is performed. Because the 100× field of view is only 30 μm on a side, there is a strong possibility of finding areas at the end of a blood smear 61 (FIG. 10) that have no cells in a field of that size. If focus cannot be achieved, it is assumed that this corner is empty and the hypothetical rectangle 63 (FIG. 10B) is contracted towards the lower left corner in 30 μm increments until an occupied corner is encountered.

The slide then moves to the upper right corner of the hypothetical rectangle 63 (FIG. 10B); where again a long focus is done and it is determined if the corner is occupied. However, this time if the corner is empty the rectangle width is contracted towards the left in 30 μm increments, until an occupied corner is encountered.

Finally, the lower right corner, which is guaranteed to be occupied, undergoes long focusing as does the center of the Optimal Examination Area. These points are then employed to create the focal map, which is used to compute the focus, z, for any given point (x,y) as the stage moves.

Under this higher magnification the x-y plane is not as flat as it is under the lower magnification. The focal plane map is much more accurate over short distances than large ones. Fortunately, the distance traveled between the cells during imaging is small compared to the width and height of the hypothetical rectangle 63. To take advantage of this and for improved accuracy, the algorithm computes the linear change in z over the distance between the last imaged cell and the closest corner of the focal map, rather than over entire focal map.

Figure 21:
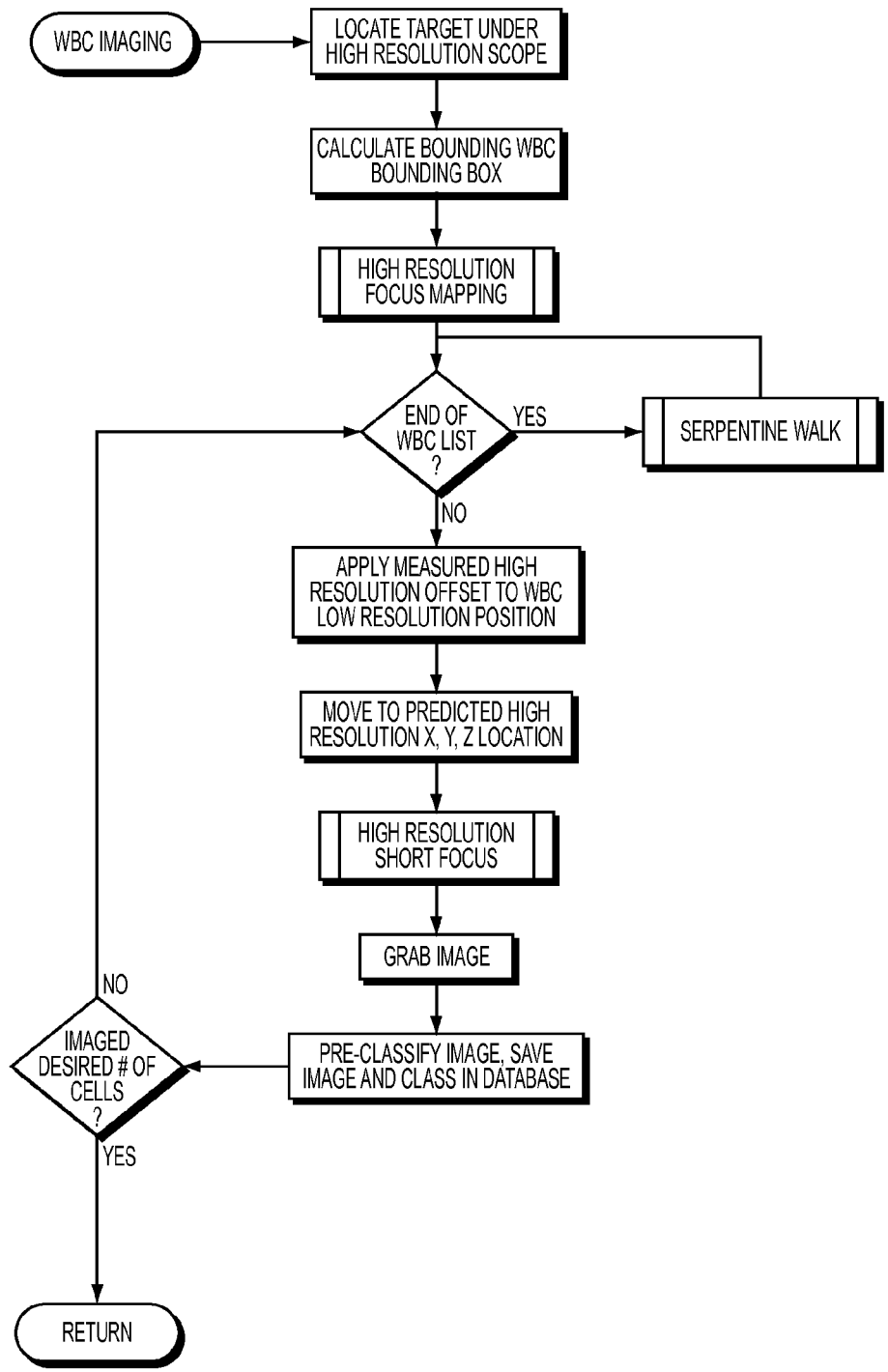
FIG. 21 is a Flow Chart for White Blood Cell Imaging.

FIG. 21, digital images of the cells are acquired and sent to the computer for image analysis. Cells of interest are grouped by color, size and morphological characteristics; preclassified and ultimately reviewed and verified by a trained technician.

Figure 22:
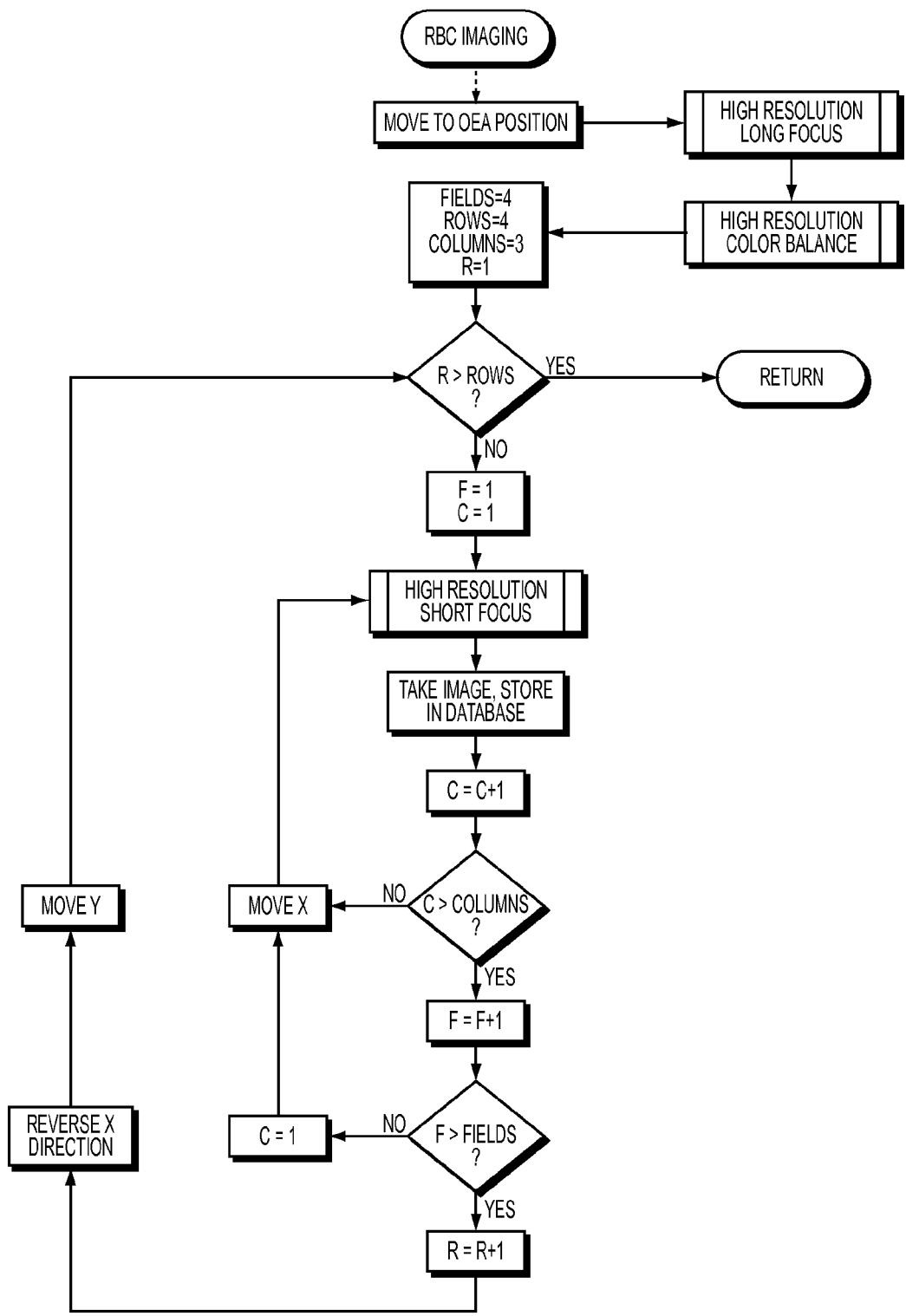
FIG. 22 is a Flow Chart for Red Blood Cell Morphology Imaging.

FIG. 22, when a blood test is done manually, in addition to the white blood cells, the technician does a gross evaluation of the morphology of the red blood cells. If a number of red blood cell anomalies are seen, the technician examines the red blood cells under 50×. Normally four areas, encompassing approximately 1000 cells are examined by the technician. The current apparatus approximates this operation.

Employing the 100× objective, the same starting point, the center of red blood cell maximum count, is used to start the imaging process. The fields, in total, approximate the same area as the 50× fields that are done by a manual microscope. The images are tiled and presented to the technician as a mosaic for evaluation.

Figure 23:
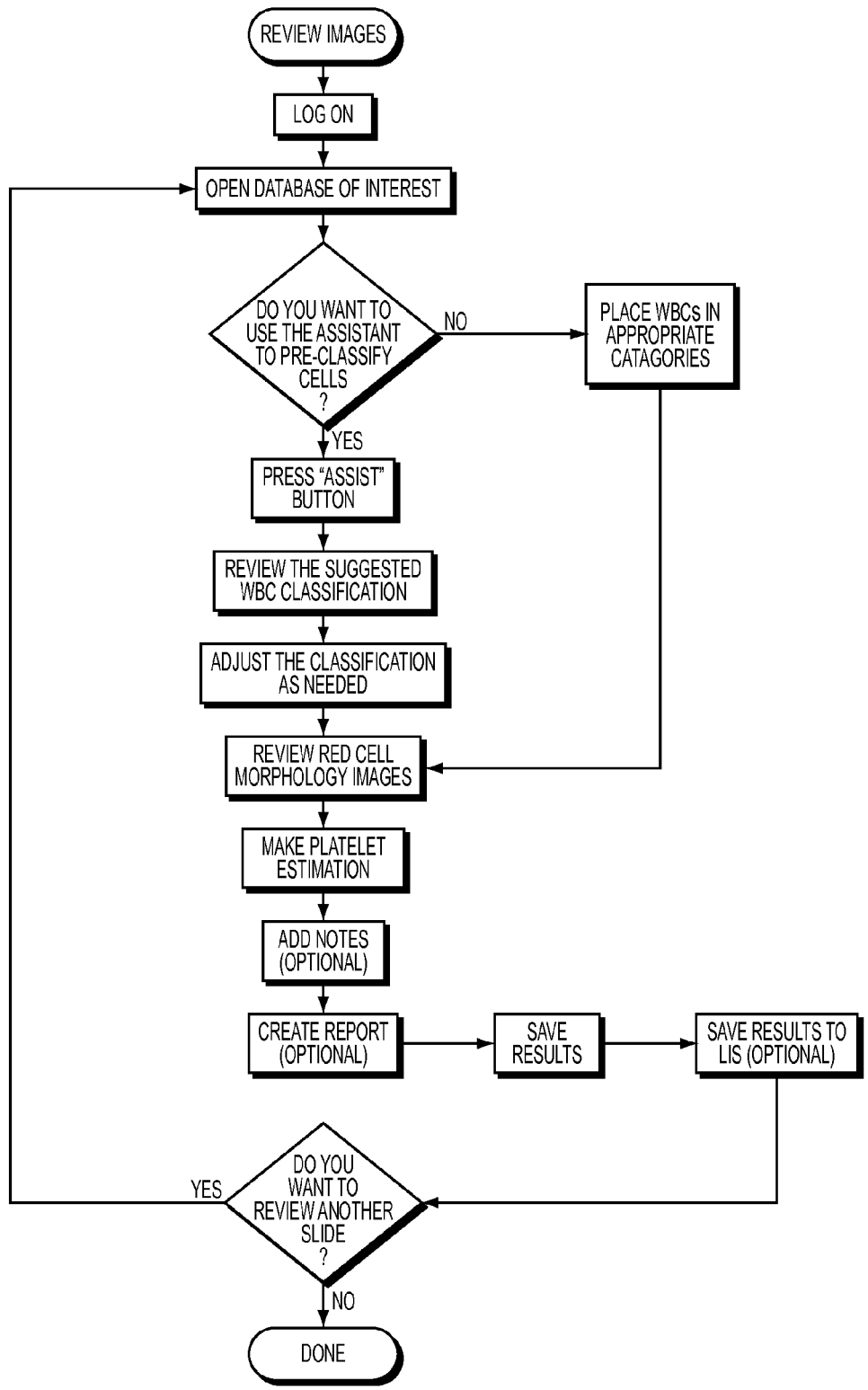
FIG. 23 Is a Flow Chart for Image Review.

FIG. 23, the system allows the technician to choose how the technician wishes to work with the data acquired by the Easy Cell system. The technician may work with the pre-classification system or review and adjust the classifications presented. The technician also has the opportunity to make comments about the images and store these comments with the images.

DRAWINGS

| FIGURE | Title |
| --- | --- |
| 1 | Easy Cell System |
| 2A | Oiling Device |
| 2B | Oiling Device, side removed |

| DRAWINGS | | |
|---|---|---|
| FIGURE | Title | |
| 3 | Carousel | |
| 4 | Easy Cell, housing removed | |
| 5 | X-Y Carriage | |
| 6A | Gripper, top plate removed. | |
| 6B | Fixed Optical Target | |
| 7A | Microscope Sub Assembly | |
| 7b | High Powered Microscope, side view | |
| 8 | LED with coiled fiber optics | |
| 9 | STAT Access Assembly | |
| 10A | Microscope Slide with Hypothetical Diamond | |
| 10B | Microscope Slide with Hypothetical Rectangle | |
| 11 | Flow Chart for the Overall Process | |
| 12 | Flow Chart for Slide Retrieval | |
| 13 | Flow Chart for Processing the Retrieved Slide | |
| 14 | Flow Chart for Optical Examination Area | |
| 15 | Flow Chart for Long Focus Operation | |
| 16 | Flow Chart for Short Focus Operation | |
| 17 | Flow Chart for Low Resolution Focus Mapping | |
| 18 | Flow Chart for Serpentine Walk | |
| 19 | Flow Chart for Low Resolution Image Evaluation | |
| 20 | Flow Chart for High Resolution Focus Mapping | |
| 21 | Flow Chart for White Blood Cell Imaging | |
| 22 | Flow Chart for Red Blood Cell Morphology Imaging | |
| 23 | Flow Chart for Image Review | |

| Number | Descriptor |
|---|---|
| 1 | Easy Cell Housing |
| 2 | Carousel Portal |
| 3 | STAT Access Slot |
| 4 | Access Panel |
| 5 | Oiling Device |
| 6 | Computer |
| 7 | Monitor |
| 8 | Keyboard |
| 9 | Mouse |
| 10 | Oiling Device Access Slot |
| 11 | Immersion Oil Well |
| 12 | Applicator |
| 13 | Wiper |
| 14 | Carousel |
| 15 | Receiving Clip Carousel |
| 16 | Indexing Slot |
| 17 | X,Y Carriage |
| 18 | Carousel Housing |
| 19 | Center Rail (Y Direction) |
| 20 | Center Rail (X Direction) |
| 21 | Linear Bearings (X Direction) |
| 22 | Shock Absorbers |
| 23 | Zanite Base |
| 24 | Gripper |
| 25 | STAT Access Assembly |
| 26 | Low Power Microscope |
| 27 | High Power Microscope |
| 28 | Microscope Tower |
| 29 | Digital Cameras |
| 30 | Bar Code Reader/Camera |
| 31 | Linear Induction Motor, X-Direction |
| 32 | Linear Induction Motor, Y-Direction |
| 33 | Y Encoder |
| 34 | X Encoder |
| 35 | Y Encoder Strip |
| 36 | X Encoder Strip |
| 37 | Linear Bearing (Y Direction) |
| 38 | Gripper Arm with Fixed Optical Target |
| 39 | Gripper Arm |
| 40 | Servomotor for Gripper |
| 41 | Cam for Gripper |
| 42 | Spring for Gripper |
| 43 | Fixed Optical Target |
| 44 | Objective Carriage |
| 45 | Low Power Microscope Objective |
| 46 | High Power Microscope Objective |
| 47 | Low Power Microscope Light Condenser |
| 48 | High Power Microscope Light Condenser |
| 49 | Voice Coil |
| 50 | Springs |
| 51 | Linear Cross Bearing |
| 52 | Fiber Optic Attachment |
| 53 | LED |
| 54 | Coiled Fiber Optics |
| 55 | LED Fiber Optics, sub stage end |
| 56 | Receiving Clip STAT Assembly |
| 57 | Solenoid STAT Assembly |
| 58 | Trip Switch STAT Assembly |
| 59 | Servo Motor STAT Assembly |
| 60 | Microscope Slide |
| 61 | Blood Smear |
| 62 | Hypothetical Diamond |
| 63 | Hypothetical Rectangle |

We claim:

1. An apparatus for analyzing stained blood cells on a microscope slide which comprises:
   (a) a computer comprising;
      i. a processor;
      ii. random access memory;
      iii. a monitor in communication with the computer; and
      iv. an input device in communication with the computer;
   (b) a base having a flat surface lying in the X-Y plane;
   (c) a gripper to acquire and transport the microscope slides and which serves as a microscope stage; the gripper being constrained to move in the X-Y plane
   (d) a motor to move the gripper in the X direction;
   (e) a motor to move the gripper in the Y direction;
   (f) a microscope tower fixed with respect to the base
   (g) two microscopes with optical axes lying parallel to the Z direction, wherein the microscopes have upper parts attached to the microscope tower and lower parts comprising objectives of different powers and aligned to the optical axes, the lower parts being constrained to move in the z direction along their optical axes,
   (h) wherein a first of the two upper parts is aligned with a first of the objectives along a first of the optical axes,
   (i) wherein a second of the two upper parts is aligned with a second of the objectives along a second of the optical axes,
   (i) wherein the motors allow the gripper to move a cell located on the slide under either the first or second aligned microscope objectives;
   (k) at least one focusing actuator for moving the two microscope objectives in the Z direction; and
   (l) a light source to illuminate the microscope slides.

2. An apparatus as in claim 1, in which the computer has a system processor comprising at least 2.4 GHz.

3. An apparatus as in claim 1, in which the computer random access memory comprises at least 512 MB.

4. An apparatus as in claim 1, in which the computer input device comprises at least one of a keyboard, mouse, roller ball, or touch screen.

5. An apparatus as in claim 1, further including a carousel with multiple slots for the microscope slides and wherein the gripper is operative to acquire the microscope slides from the carousel.

6. An apparatus as in claim 1, further including a reader to capture an identifier on an end of each microscope slide.

7. An apparatus as in claim 6, wherein the reader is an electronic camera capable of interpreting a bar code.

8. An apparatus as in claim 1, in which the stage motors comprise linear induction motors, which are optically encoded to a strip fixed to the base.

9. An apparatus as in claim 8, in which the stage motors move reliably and accurately to within about 0.5 microns.

10. An apparatus as in claim 1, in which the gripper to acquire and transport microscope slides comprises:
 a. a lever having a forked end;
 b. the forked end comprising spaced apart furcations;
 c. each furcation is pinned pivotally at two points to a cam, which is controlled by a servo motor to turn the cam to open and close the furcations; and
 d. the furcations are bridged with a spring to keep them under tension.

11. An apparatus as in claim 10, in which one of the furcations has sufficient free play, approximately 0.05 inches, to accommodate microscope slides of differing widths.

12. An apparatus as in claim 1, in which the light source includes an LED source and fiber optics, and wherein light conducted by the fiber optics from the LED source is shaped by light condensers.

13. An apparatus as in claim 12, in which the fiber optics are looped to eliminate anisotropy from the LED light source.

14. An apparatus as in claim 1, in which the focusing actuator for moving the objectives in the Z axis is a voice coil, a coil portion of which is attached to the microscope tower, and the magnetic portion of which is attached to an objective carriage for the objectives and wherein the coil is under positive tension from at least one extension spring, and optically encoded to a strip fixed to the base.

15. An apparatus as in claim 14, in which the voice coil is capable of focusing reliably to within about 20 nm resolution.

16. The apparatus as in claim 1, further including means to establish an initial focus of the microscopes including a fixed target comprising a clear window, with a black dot in the center surrounded by clear concentric rings, affixed to a fixed arm of the gripper.

17. The apparatus as in claim 1, further including a means of introducing a single slide for priority analysis.

18. The apparatus as in claim 1, further including at least one camera in communication with the computer to capture digital images from the two microscopes.

* * * * *